(12) United States Patent
Cong et al.

(10) Patent No.: US 10,495,616 B2
(45) Date of Patent: Dec. 3, 2019

(54) METHOD TO INCREASE THE CHROMATOGRAPHIC RESOLUTION OF OLEFIN-BASED POLYMERS WITH DIFFERENT MICROSTRUCTURES

(71) Applicant: Dow Global Technologies LLC, Midland, MI (US)

(72) Inventors: Rongjuan Cong, Lake Jackson, TX (US); Albert Parrott, Lake Jackson, TX (US); Cherry Hollis, Freeport, TX (US)

(73) Assignee: Dow Global Technologies LLC, Midland, MI (US)

(*) Notice: Subject to any disclaimer, the term of this patent is extended or adjusted under 35 U.S.C. 154(b) by 35 days.

(21) Appl. No.: 15/752,323

(22) PCT Filed: Aug. 30, 2016

(86) PCT No.: PCT/US2016/049399
§ 371 (c)(1),
(2) Date: Feb. 13, 2018

(87) PCT Pub. No.: WO2017/040473
PCT Pub. Date: Mar. 9, 2017

(65) Prior Publication Data
US 2019/0049416 A1 Feb. 14, 2019

Related U.S. Application Data

(60) Provisional application No. 62/212,930, filed on Sep. 1, 2015.

(51) Int. Cl.
| | | |
|---|---|---|
| G01N 30/88 | (2006.01) | |
| G01N 30/30 | (2006.01) | |
| G01N 30/54 | (2006.01) | |
| B01D 15/16 | (2006.01) | |
| B01D 15/34 | (2006.01) | |
| B01D 9/00 | (2006.01) | |
| G01N 30/32 | (2006.01) | |

(52) U.S. Cl.
CPC ........... *G01N 30/88* (2013.01); *B01D 15/161* (2013.01); *B01D 15/34* (2013.01); *G01N 30/30* (2013.01); *G01N 30/54* (2013.01); *B01D 9/0013* (2013.01); *G01N 2030/3076* (2013.01); *G01N 2030/324* (2013.01); *G01N 2030/885* (2013.01)

(58) Field of Classification Search
USPC ....................................................... 528/502
See application file for complete search history.

(56) References Cited

U.S. PATENT DOCUMENTS

| | | |
|---|---|---|
| 4,798,081 A | 1/1989 | Hazlitt et al. |
| 7,985,593 B2 | 7/2011 | Gillespie et al. |
| 8,076,147 B2 | 12/2011 | Damme et al. |
| 8,318,896 B2 | 11/2012 | Winniford et al. |
| 9,095,792 B2 | 8/2015 | Winniford et al. |
| 2008/0166817 A1 | 7/2008 | Gillespie et al. |
| 2011/0152499 A1 | 6/2011 | Winniford et al. |
| 2014/0090453 A1 | 4/2014 | Cong et al. |

FOREIGN PATENT DOCUMENTS

| | | |
|---|---|---|
| EP | 2008701 A2 | 12/2008 |
| EP | 2859926 A2 | 4/2015 |
| JP | 2013133451 A | 7/2013 |
| JP | 2016080415 A | 5/2016 |
| WO | 2004034047 A1 | 4/2004 |
| WO | 2010042389 A2 | 4/2010 |
| WO | 2012166861 A1 | 12/2012 |
| WO | 2017040473 A1 | 3/2017 |
| WO | 2017058627 A1 | 4/2017 |

OTHER PUBLICATIONS

Alghyamah et al., Macromolecular Chemistry and Physics, 2014, 215, 465.
Alghyamah et al., Macromolecular Chemistry and Physics, 2015, 216, 38.
Cong, et al., Macromolecules, 11, 44 (8), 3062.
Cong, et al., Method of Continuous Background Referencing Applied to Differential Detectors for High Performance Liquid Chromatography (HPLC), http://priorart.ip.com/IPCOM/000232437, pp. 1-3.
Giddings (1990), Use of Multiple Dimensions in Analytical Separations, in Hernan Cortes Editor, Multidimensional Chromatography: Techniques and Applications (1st ed. pp. 1), New York, NY: Marcel Dekker, Inc.
Hazlitt, Lonnie G., "Determination of Short-Chain Branching Distributions of Ethylene Copolymers by Autoated Analytical Temperature Rising Elution Fractionation", Journal of Applied Polymer Science: Applied Polymer Symposium, 1990, 45, 25-37.
Williams et al., "The Construction of a Polyethylene Calibration Cure for Gel Permeation Chromatography Using Polystyrene Fractions", Polymer Letters, 1968, 621-624.
International Search Report and Written Opinion pertaining to PCT/US2016/049399 dated Nov. 22, 2016.
International Search Report and Written Opinion pertaining to PCT/US2016/048268 dated Nov. 8, 2016.

*Primary Examiner* — Terressa Boykin
(74) *Attorney, Agent, or Firm* — Dinsmore & Shohl LLP

(57) ABSTRACT

A method increase of the Resolution Index (RI) of a chromatogram generated from a polymer sample comprising at least two olefin-based polymers of different microstructures and/or at least two olefin-based polymer fractions of different microstructures. The method comprises separating the mixture on a low-porosity stationary phase and repeatedly cycling the sample-stationary phase through a series of cooling and heating stages with active eluent flow only during the cooling stages and during the last heating stage to elute the separated analytes off the column.

17 Claims, 7 Drawing Sheets

METHOD TO INCREASE THE CHROMATOGRAPHIC RESOLUTION OF OLEFIN-BASED POLYMERS WITH DIFFERENT MICROSTRUCTURES

REFERENCE TO RELATED APPLICATIONS

The present application claims the benefit of U.S. Provisional Application No. 62/212,930, filed on Sep. 1, 2015, and incorporated herein by reference.

BACKGROUND OF THE INVENTION

Comonomer content and distribution (CCD), also often called the short chain branching distribution (SCBD) is one of the key parameters controlling olefin-based polymer properties. A precise and accurate CCD analysis is critical for new product development. Current techniques use crystallization based (CEF, for example, see Monrabal and Mayo et al., Macromolecular Symposia, 2012; and TREF) or interaction based techniques (high temperature thermal gradient interaction chromatography, HT-TGIC, or a short abbreviation as TGIC (for example, see Cong and deGroot et al., Macromolecules, 2011, 44, 3062) to measure CCD. However, these techniques have the following shortcomings: limited resolution, one plate separation, and coelution/cocrystallization.

The most challenging issue in CEF, and all the other crystallization based separation techniques, is the co-crystallization (for example, see Alghyamah and Soares, Macromolecular Chemistry and Physics, 2014, 215, 465; & Macromolecular Chemistry and Physics, 2015, 216, 38), which leads to an error in SCBD results. On the other hand, the accuracy of HT-TGIC of olefin-based polymers is reduced because of poor resolution and coelution issues. These challenges make accurate SCBD modeling very difficult to achieve. Thus, there is a need for new chromatography techniques that improve resolution, and thus the accuracy, of a CCD (or SCBD) analysis. This need has been met by the following invention.

SUMMARY OF THE INVENTION

A method is provided to increase of the Resolution Index (RI) of a chromatogram generated from a polymer sample comprising at least two olefin-based polymers of different microstructures and/or at least two olefin-based polymer fractions of different microstructures;

said method comprising at least the following steps, and wherein one of A) or B) occurs:

A) n'=0, and steps d) and e) below are skipped, such that step f) follows step c), and wherein $T3_0$ is greater than $T1_0$;

B) n' is an integer ≥1; steps d) and e) are not skipped; and steps d) and e) are repeated for n'>1;

a1) dissolving the polymer sample in at least one solvent to form a polymer solution;

a2) injecting at least a portion of the polymer solution onto a stationary phase at a temperature $T1_0$ (in ° C.), and wherein no eluent flow through the stationary phase;

b) setting a constant eluent flow rate ($FR_0$) through the stationary phase, while simultaneously cooling the stationary phase at a cooling rate $CR_0$, to a minimum temperature $T2_0$ (in ° C.), where $T2_0 < T1_0$; and wherein the flow of the eluent through the stationary phase is stopped at temperature $T2_0$;

c) when the temperature reaches $T2_0$, optionally maintaining the temperature at $T2_0$ for a time $t_{20}$; increasing the temperature of the stationary phase to $T3_0$, at a heating rate $HR_0$, where $T3_0 > T2_0$, while maintaining no flow of eluent through the stationary phase; and when the temperature reaches temperature $T3_0$, maintaining no flow rate through the stationary phase a time $t_{30}$; and maintaining the temperature at $T3_0$ for the time $t_{30}$;

wherein for steps d) and e) below, at each n value, where n is from 1 to n', the eluent flow rate of step d) is $FR_n$; and wherein at least one $T3_n$ (for n≥1) is greater than $T1_0$;

d) setting a constant eluent flow rate ($FR_n$) through the stationary phase, while simultaneously cooling the stationary phase at a rate $CR_n$, to a minimum temperature $T2_n$, where $T2_n < T3_{n-1}$; and wherein the flow of the eluent through the stationary phase is stopped at temperature $T2_n$;

e) when the temperature reaches $T2_n$, optionally maintaining the temperature at $T2_n$ for a time $t_{2n}$; increasing the temperature of the stationary phase to $T3_n$, at a heating rate $HR_n$, where $T3_n > T2_n$, while maintaining no flow of eluent through the stationary phase; and when the temperature reaches temperature $T3_n$, maintaining no flow rate through the stationary phase for a time $t_{3n}$; and maintaining the temperature of the stationary phase at $T3_n$ for the time $t_{3n}$;

f) setting a constant eluent flow rate ($FR_f$) through the stationary phase, while simultaneously cooling the stationary phase at a rate $CR_f$ to a temperature $T2_f$ and when the temperature reaches temperature $T2_f$ optionally maintaining the temperature at $T2_f$ for a time $t_{2f}$;

g) increasing the flow rate ($FR_e$) of the eluent through the stationary phase to at least 0.1 ml/min, while increasing the temperature of the stationary phase to $T_f$ ($T_f > T2_f$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the chromatogram; and wherein the resolution index (RI)=((RC−R0)/R0)×100; and where RI>zero; and wherein RC is the difference in the elution times of two peak height maximums on the chromatogram; and wherein R0 is the difference in the elution times of the same two peaks height maximums selected for the determination of RC, and wherein these two peak height maximums are present on a comparative chromatogram, generated under the same conditions as the chromatogram for RC, except that the following steps were used in the analysis:

c1) injecting at least a portion of the polymer solution onto a stationary phase at a temperature $T1_0$ (in ° C.), and wherein no eluent flow through the stationary phase;

c2) setting a constant eluent flow rate ($FR_0$) through the stationary phase, while simultaneously cooling the stationary phase at a cooling rate $CR_0$, to a minimum temperature $T2_0$ (in ° C.), where $T2_0 < T1_0$; and wherein the flow of the eluent through the stationary phase is stopped at temperature $T2_0$, optionally maintaining the temperature at $T2_0$ for a period $t_{20}$;

c3) increasing the flow rate ($FR_e$) of the eluent through the stationary phase at a rate of at least 0.1 ml/min, while increasing the temperature of the stationary phase to $T_f$ ($T_f > T2_0$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the comparative chromatogram.

DETAILED DESCRIPTION

Figure 1:
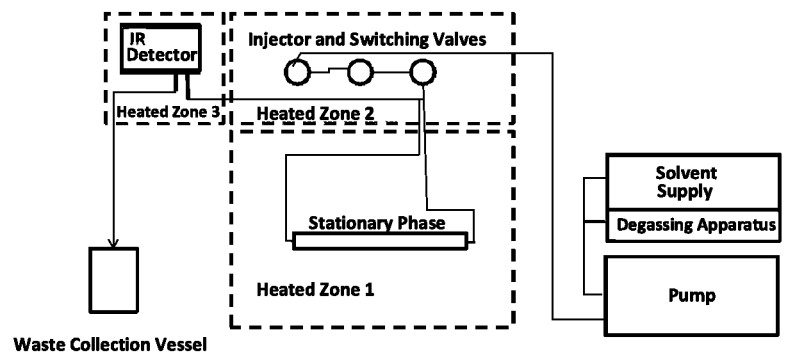
FIG. 1 depicts a schematic drawing of HT-TGIC set up.

It has been discovered that the use of a modulated thermal gradient profile, as described herein, covering the entire range of adsorption temperature, dramatically improves resolution and accuracy of a chromatographic resolution of olefin-based polymers and/or polymer fractions, and thus provides a more accurate CCD and/or SCBD analysis. The improvement leads to a dramatic improvement in characterization of the microstructure of olefin-based polymers as compared to current CEF, TREF, HT-TGIC, cross fractionation and TGIC-hyphenated GPC (TGIC-h-GPC) techniques.

As discussed above, a method is provided to increase of the Resolution Index (RI) of a chromatogram, and preferably a chromatogram generated by HT-TGIC, generated from a polymer sample comprising at least two olefin-based polymers of different microstructures and/or at least two olefin-based polymer fractions of different microstructures;

said method comprising at least the following steps, and wherein one of A) or B) occurs (here, n' represents the number of times step d), followed by step e), is performed):

A) n'=0, and steps d) and e) below are skipped, such that step f) follows step c), and wherein $T3_0$ is greater than $T1_0$;

B) n' is an integer ≥1; steps d) and e) are not skipped; and steps d) and e) are repeated for n'>1 [i.e., for n'=1, steps d) and e) are not skipped; and for n'>1, steps d) and e) are not skipped, and steps d) and e) are repeated for n'−1 times, before step f)];

a1) dissolving the polymer sample in at least one solvent to form a polymer solution;

a2) injecting at least a portion of the polymer solution onto a stationary phase at a temperature $T1_0$ (in ° C.), and wherein no eluent flow through the stationary phase;

b) setting a constant eluent flow rate ($FR_0$) through the stationary phase, while simultaneously cooling the stationary phase at a cooling rate $CR_0$, to a minimum temperature $T2_0$ (in ° C.), where $T2_0 < T1_0$; and wherein the flow of the eluent through the stationary phase is stopped at temperature $T2_0$;

c) when the temperature reaches $T2_0$, optionally maintaining the temperature at $T2_0$ for a time $t_{20}$; increasing the temperature of the stationary phase to $T3_0$, at a heating rate $HR_0$, where $T3_0 > T2_0$, while maintaining no flow of eluent through the stationary phase; and when the temperature reaches temperature $T3_0$, maintaining no flow rate through the stationary phase a time $t_{30}$; and maintaining the temperature at $T3_0$ for the time $t_{30}$;

wherein for steps d) and e) below, at each n value, where n is from 1 to n', the eluent flow rate of step d) is $FR_n$; and wherein at least one $T3_n$ (for n≥1) is greater than $T1_0$;

d) setting a constant eluent flow rate ($FR_n$) through the stationary phase, while simultaneously cooling the stationary phase at a rate $CR_n$, to a minimum temperature $T2_n$, where $T2_n < T3_{n-1}$; and wherein the flow of the eluent through the stationary phase is stopped at temperature $T2_n$;

e) when the temperature reaches $T2_n$, optionally maintaining the temperature at $T2_n$ for a time $t_{2n}$; increasing the temperature of the stationary phase to $T3_n$, at a heating rate $HR_n$, where $T3_n > T2_n$, while maintaining no flow of eluent through the stationary phase; and when the temperature reaches temperature $T3_n$, maintaining no flow rate through the stationary phase for a time $t_{3n}$; and maintaining the temperature of the stationary phase at $T3_n$ for the time $t_{3n}$;

f) setting a constant eluent flow rate ($FR_f$) through the stationary phase, while simultaneously cooling the stationary phase at a rate $CR_f$ to a temperature $T2_f$, and when the temperature reaches temperature $T2_f$, optionally maintaining the temperature at $T2_f$ for a time $t_{2f}$;

g) increasing the flow rate ($FR_e$) of the eluent through the stationary phase to at least 0.1 ml/min, while increasing the temperature of the stationary phase to $T_f$ ($T_f > T2_f$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the chromatogram; and wherein the resolution index (RI)=((RC−R0)/R0)×100; and where RI>zero; and wherein RC is the difference in the elution times of two peak height maximums on the chromatogram; and wherein R0 is the difference in the elution times of the same two peaks height maximums selected for the determination of RC, and wherein these two peak height maximums are present on a comparative chromatogram, generated under the same conditions as the chromatogram for RC, except that the following steps were used in the analysis:

c1) injecting at least a portion of the polymer solution onto a stationary phase at a temperature $T1_0$ (in ° C.), and wherein no eluent flow through the stationary phase;

c2) setting a constant eluent flow rate ($FR_0$) through the stationary phase, while simultaneously cooling the stationary phase at a cooling rate $CR_0$, to a minimum temperature $T2_0$ (in ° C.), where $T2_0 < T1_0$; and wherein the flow of the eluent through the stationary phase is stopped at temperature $T2_0$, optionally maintaining the temperature at $T2_0$ for a period $t_{20}$;

c3) increasing the flow rate ($FR_e$) of the eluent through the stationary phase at a rate of at least 0.1 ml/min, while increasing the temperature of the stationary phase to $T_f$ ($T_f > T2_0$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the comparative chromatogram.

An inventive method may comprise a combination of two or more embodiments as described herein.

The increase in the Resolution Index (RI) is indicated by an RC>R0, wherein RC and R0 are described above.

Each temperature, $T1_0$, $T2_0$, $T3_0$, etc., is the temperature of the stationary phase, which typically is the air temperature of the convection oven, in which the stationary phase is located.

An example schematic drawing of the set up for an inventive analysis is shown in FIG. 1.

In one embodiment, n'≥1, and for each n value, where n is from 1 to n', a TLVSP (calculated) meets the following Equation B:

$$TLVSPcalc. = \frac{T1_0 - T2_0}{CR_0} * FR_0 + \left\{ \sum_{1}^{n'} \left[ \frac{T3_i - T2_i}{CR_i} * FR_i \right] \right\} + \frac{T3_n - T2_f}{CR_f} * FR_f, \quad \text{(EQN B)}$$

wherein i=1 to n'; TLVSP (calculated) is the calculated Total Liquid Volume of the Stationary Phase (in units of "ml"); and wherein TLVSP (calculated)≤TLVSP (measured); wherein TLVSP (measured) is the measured Total Liquid Volume of the Stationary Phase (in units of "ml").

In one embodiment, n'=0, and a TLVSP (calculated) meets the following Equation A:

$$TLVSPcalc. = \frac{T1_0 - T2_0}{CR_0} * FR_0 + \frac{T3_0 - T2_f}{CR_f} * FR_f, \quad \text{(EQN A)}$$

wherein TLVSP (calculated) is the calculated Total Liquid Volume of the Stationary Phase (in units of "ml"); and wherein TLVSP (calculated)≤TLVSP (measured); wherein TLVSP (measured) is the measured Total Liquid Volume of the Stationary Phase (in units of "ml").

In one embodiment, the RI is ≥2%, or ≥3%, or ≥4%, or ≥5%, or ≥6%, or ≥7%, or ≥8%, or ≥9%, or ≥10%.

In one embodiment, the RI is ≥12%, or ≥13%, or ≥14%, or ≥15%, or ≥16%, or ≥17%, or ≥18%, or ≥19%, or ≥20%, or ≥21%, or ≥22%, or ≥23%, or ≥24%, or ≥25%, or ≥26%, or ≥27%, or ≥28%, or ≥29%.

In one embodiment, the RI is ≥30%, or ≥35%, or ≥40%, or ≥45%, or ≥50%, or ≥55%, or ≥60%, or ≥65%, or ≥70%, or ≥75%, or ≥80%, or ≥85%, or ≥90%, or ≥95%, or ≥100%.

In one embodiment, the stationary phase has a porosity ≤25%, or ≤20%, or ≤19%, or ≤18%, or ≤17%, or ≤16%, or ≤15%, or ≤14%, or ≤13%, or ≤12%.

In one embodiment, the stationary phase has a total pore area ≤10.0 m$^2$/g, or ≤9.0 m$^2$/g, or ≤8.0 m$^2$/g, or ≤7.0 m$^2$/g, or ≤6.0 m$^2$/g, or ≤5.0 m$^2$/g, or ≤4.0 m$^2$/g.

In one embodiment, the stationary phase has a BET surface area ≤20.0 m$^2$/g, or ≤19.0 m$^2$/g, or ≤18.0 m$^2$/g, or ≤17.0 m$^2$/g, or ≤16.0 m$^2$/g, or ≤15.0 m$^2$/g, or ≤14.0 m$^2$/g, or ≤13.0 m$^2$/g, or ≤12.0 m$^2$/g, or ≤11.0 m$^2$/g, or ≤10.0 m$^2$/g, or ≤9.0 m$^2$/g, or ≤8 m$^2$/g.

In one embodiment, the stationary phase has a $D_{50}$ value ≤200 μm, or ≤100 μm, or ≤90 μm, or ≤80 μm, or ≤70 μm, or ≤60 μm, or ≤50 μm, or ≤40 μm, or ≤30 μm, or ≤20 μm.

In one embodiment, the support material has $D_{50} \geq 2$ microns, or ≥5 microns.

In one embodiment, the support material has a $D_{50} < 28$ μm, or <25 μm.

In one embodiment, the support material has a $D_{50}$ from 2 to 30 microns, further from 5 to 30 microns, further from 5 to 25 microns.

In one embodiment, the stationary phase comprises graphitic carbon, molybdenum sulfide, or silicon carbide.

In one embodiment, n' is greater than 0, further greater than 1, further greater than 2, further greater than 3.

In one embodiment, n' is from 1 to 10, or from 1 to 8, or from 1 to 6.

In one embodiment, n' is from 1 to 5, or from 1 to 4, or from 1 to 3, or from 1 to 2.

In one embodiment, the RI value increases as n' increases.

In one embodiment, for step b) and step c2), $CR_0$ is selected from 0.1° C./min to 15.0° C./min, or from 0.1° C./min to 12.0° C./min, or from 0.1° C./min to 10.0° C./min, or from 0.1° C./min to 8.0° C./min, or from 0.1° C./min to 5.0° C./min.

In one embodiment, for step b) and step c2), $CR_0$ is selected from 1.0° C./min to 15.0° C./min, or from 1.0° C./min to 12.0° C./min, or from 1.0° C./min to 10.0° C./min, or from 1.0° C./min to 8.0° C./min, or from 1.0° C./min to 5.0° C./min.

In one embodiment, for step c), $HR_0$ is selected from 1.0° C./min to 100° C./min, further from 1.0° C./min to 50° C./min, further from 1.0° C./min to 20° C./min, further from 1.0° C./min to 10° C./min, further from 1.0° C./min to 5.0° C./min.

In one embodiment, for step c), $t_{30}$ is ≥1.0 minute, further ≥2.0 minutes, further ≥3.0 minutes, further ≥4.0 minutes, further ≥5.0 minutes, further ≥6.0 minutes, further ≥7.0 minutes, further ≥8.0 minutes, further ≥9.0 minutes, further ≥10 minutes.

In one embodiment, for step d), $CR_n$ is selected from, 0.1° C./min to 15.0° C./min, or from 0.1° C./min to 10.0° C./min, or from 0.1° C./min to 5.0° C./min.

In one embodiment, for step d), $CR_n$ is selected from, 1.0° C./min to 15.0° C./min, or from 1.0° C./min to 10.0° C./min, or from 1.0° C./min to 5.0° C./min.

In one embodiment, for step e), $HR_n$ is from 1.0° C./min to 100° C./min, further from 1.0° C./min to 50° C./min, further from 1.0° C./min to 20° C./min, further from 1.0° C./min to 10° C./min, further from 1.0° C./min to 5.0° C./min.

In one embodiment, for step e), $t_{3n}$ is ≥1.0 minute, further ≥2.0 minutes, further ≥3.0 minutes, further ≥4.0 minutes, further ≥5.0 minutes, further ≥6.0 minutes, further ≥7.0 minutes, further ≥8.0 minutes, further ≥9.0 minutes, further ≥10 minutes.

In one embodiment, for step f), the $CR_f$ is selected from 0.1° C./min to 5.0° C./min, further from 0.1° C./min to 4.0° C./min, further from 0.1° C./min to 3.0° C./min.

In one embodiment, for step f), the $CR_f$ is selected from 1.0° C./min to 5.0° C./min, further from 1.0° C./min to 4.0° C./min, further from 1.0° C./min to 3.0° C./min.

In one embodiment, for step f), the $t_{2f}$ is ≥1.0 minute, further ≥2.0 minutes.

In one embodiment, for step f), the $t_{2f}$ is ≥100 minute, further ≤50 minutes, further ≤20 minutes, further ≤10 minutes.

In one embodiment, the at least two olefin-based polymers have different short chain branching distributions and/or at least two olefin-based polymer fractions have different short chain branching distributions.

In one embodiment, the polymer sample comprises at least two olefin-based polymers that have different short chain branching distributions.

In one embodiment, the polymer sample comprises at least two olefin-based polymer fractions that have different short chain branching distributions.

In one embodiment, the polymer sample comprises at least two olefin-based polymers, and wherein each olefin-based polymer is independently selected from the following: an ethylene-based polymer or a propylene-based polymer. The two polymers are prepared using different catalyst systems and/or different polymerization conditions (for example, temperature, pressure, monomer levels and/or hydrogen level). For examples, in-situ polymer blends, and post-reactor polymer blends.

In one embodiment, the polymer sample comprises at least two olefin-based polymers, and wherein each olefin-based polymer is independently selected from the following: an ethylene/α-olefin interpolymer, a propylene/α-olefin interpolymer, or a propylene/ethylene interpolymer.

In one embodiment, the polymer sample comprises at least two olefin-based polymers, and wherein each olefin-based polymer is independently selected from the following: an ethylene/α-olefin copolymer, a propylene/α-olefin copolymer, or a propylene/ethylene copolymer.

In one embodiment, the polymer sample comprises at least two olefin-based polymer fractions, and wherein each olefin-based polymer fraction is independently selected from the following: an ethylene-based polymer fraction or a propylene-based polymer fraction. A polymer fraction refers to a portion of a polymerized polymer that has a different microstructure, for example, different density, different amount of comonomer, and/or a non-continuum difference in molecular weight, as compared to another portion of the polymer, and where the polymer is prepared using one catalyst system and one set of polymerization conditions. For example, a polymer polymerized using a Ziegler-Natta catalyst system, which has a high density fraction and a low density fraction, as determined by TREF (Temperature Rising Elution Fractionation).

In one embodiment, the polymer sample comprises at least two olefin-based polymer fractions, and wherein each olefin-based polymer fraction is independently selected from the following: an ethylene/α-olefin interpolymer fraction, a propylene/α-olefin interpolymer fraction, or a propylene/ethylene interpolymer fraction.

In one embodiment, the polymer sample comprises at least two olefin-based polymer fractions, and wherein each olefin-based polymer fraction is independently selected from the following: an ethylene/α-olefin copolymer fraction, a propylene/α-olefin copolymer fraction, or a propylene/ethylene copolymer fraction.

In one embodiment, the chromatogram is generated using an interactive based chromatography analysis, for example, a temperature interactive chromatography.

In one embodiment, the chromatogram is generated using HT-TGIC.

In one embodiment, each olefin-based polymer, independently, has a density from 0.850 to 0.980 g/cc, or from 0.860 to 0.960 g/cc, or from 0.870-0.940 g/cc (1 cc=1 cm$^3$).

A temperature gradient device (for example, a GC oven (Agilent Technologies), used in a CEF from PolymerChar) is an instrument that is used to thermally treat, or cool, a column (for example, a chromatography column) in a controlled manner. Other examples are Hewlett Packard GC ovens, and ATREF ovens (for example, see Gillespie et al., U.S. 2008/0166817A1).

A solvent gradient device (for example, a dual pump system with a mixer (Agilent Technologies) as available from PolymerChar) is an instrument that is used to mix two or more solvents in a controlled manner, and wherein the solvent mixture is used as an eluent in a column (for example, a chromatography column). Examples include binary Shimadzu LC-20 AD pumps (see Roy et al, Development of Comprehensive Two-Dimensional High Temperature Liquid Chromatography x Gel Permeation Chromatography for Characterization of Polyolefins, Macromolecules 2010, 43, 3710-3720) and binary Agilent pumps from HTLC instrument (PolymerChar).

In one embodiment, the liquid flowing through the support material is a strong eluent. Examples of strong eluents include, but are not limited to, 1,2-dichlorobenzene, 1,2,4-trichlorobenzene, and tetrachloroethylene.

In one embodiment, the liquid flowing through the support material is a weak eluent. Examples of weak eluent include, but are not limited to, decanol, diphenyl ether and decane.

In one embodiment, the liquid flowing through the support material is a mixture of a strong eluent and a weak eluent. Examples of weak eluent include, but are not limited to, decanol/1,2,4-trichlorobenzene, diphenyl ether/1,2-dichlorobenzene, decane/1,2-dichlorobenzene.

In one embodiment, the polymer sample has a concentration in the solution of greater than 0.1 milligrams polymer per milliliter of solution. In a further embodiment, the polymer is an olefin-based polymer.

An inventive method can be used in a preparative scale, where a large quantity of polymer (in the term of grams, kilograms) is fractionated according to its CCD.

In one embodiment, also is provide a preparative scale production of polymer comprising an inventive method described herein.

An inventive method can be coupled, on or off line, with other analytical methods. For example, the effluent from an SEC column containing a copolymer of a selected molecular size can be analyzed by Temperature Rising Elution Fractionation (TREF), Crystallization Elution Fractionation (CEF), solvent gradient of HTLC (U.S. Pat. No. 8,076,147) or Thermal Gradient Interactive Chromatography (TGIC) to determine the comonomer ratio of the selected molecular sizes. See also Roy et al., Development of Comprehensive Two-Dimensional High Temperature Liquid Chromatography x Gel Permeation Chromatography for Characterization of Polyolefins, Macromolecules (2010), 43, 3710-3720; Gillespie et al., "APPARATUS AND METHOD FOR POLYMER CHARACTERIZATION", US2008/0166817A1; each incorporated herein by references.

Figure 11:
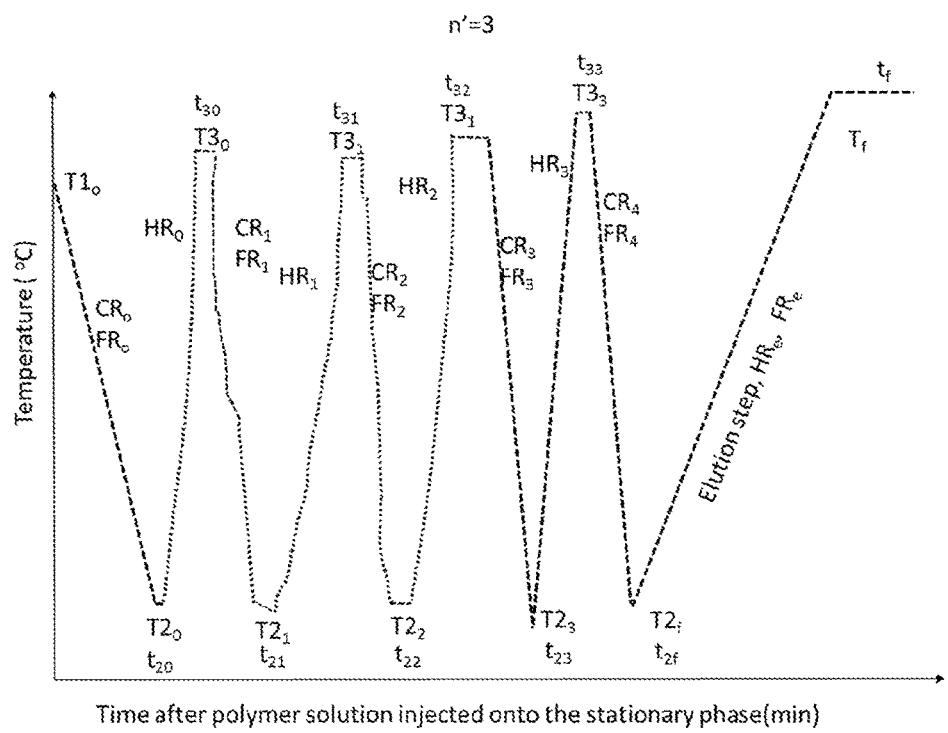
FIG. 11 depicts non-linear heating and cooling rates in a schematic temperature versus the time profile (after sample injected onto the stationary phase) for an inventive analysis.

Those skilled in the art, may use non-linear heating and cooling rates in the methods described herein. Those skilled in the art, may use non-linear flow rate at any of the heating and cooling steps in the methods described herein. For example, see FIG. 11.

An inventive method may comprise a combination of two or more embodiments as described herein.

A support material may comprise a combination of two or more embodiments as described herein.

Olefin-Based Polymers and Olefin-Based Polymer Fractions

In one embodiment, each olefin-based polymer or polymer fraction is, independently, an ethylene-based polymer or polymer fraction.

In one embodiment, each olefin-based polymer or polymer fraction is, independently, an ethylene/alpha-olefin interpolymer or interpolymer fraction. In a further embodiment, the alpha-olefin is a C3-C10 alpha-olefin, and preferably selected from propylene, 1-butene, 1-hexene, and 1-octene.

In one embodiment, each olefin-based polymer or polymer fraction is, independently, an ethylene/alpha-olefin copolymer or copolymer fraction. In a further embodiment, the alpha-olefin is a C3-C10 alpha-olefin, and preferably selected from propylene, 1-butene, 1-hexene, and 1-octene.

In one embodiment, each olefin-based polymer or polymer fraction is, independently, a propylene-based polymer or polymer fraction.

In one embodiment, each olefin-based polymer or polymer fraction is, independently, a propylene/alpha-olefin interpolymer or interpolymer fraction. In a further embodiment, the alpha-olefin is a C4-C10 alpha-olefin, and preferably selected from ethylene, 1-butene, 1-hexene, and 1-octene.

In one embodiment, each olefin-based polymer or polymer fraction is, independently, a propylene/alpha-olefin copolymer or copolymer fraction. In a further embodiment, the alpha-olefin is a C4-C10 alpha-olefin, and preferably selected from ethylene, 1-butene, 1-hexene, and 1-octene.

In one embodiment, each olefin-based polymer or polymer fraction is, independently, a propylene/ethylene interpolymer or interpolymer fraction.

In one embodiment, each olefin-based polymer or polymer fraction is, independently, a propylene/ethylene copolymer or copolymer fraction.

In one embodiment, each olefin-based polymer, or polymer fraction, independently, has a density less than, or equal to, 0.980 g/cc; or less than, or equal to, 0.970 g/cc; or less than, or equal to, 0.960 g/cc (1 cc=1 cm$^3$).

In one embodiment, each olefin-based polymer or polymer fraction, independently, has a density less than, or equal to, 0.940 g/cc; or less than, or equal to, 0.930 g/cc; or less than, or equal to, 0.920 g/cc (1 cc=1 cm$^3$).

In one embodiment, each olefin-based polymer or polymer fraction, independently, has a density less than, or equal to, 0.910 g/cc; or less than, or equal to, 0.900 g/cc; or less than, or equal to, 0.890 g/cc (1 cc=1 cm$^3$).

In one embodiment, each olefin-based polymer or polymer fraction, independently, has a density greater than, or equal to, 0.850 g/cc; or greater than, or equal to, 0.860 g/cc; or greater than, or equal to, 0.870 g/cc (1 cc=1 cm$^3$).

In one embodiment, each olefin-based polymer or polymer fraction, independently, has a density from 0.850 g/cc to 0.980 g/cc, or from 0.860 g/cc to 0.960 g/cc, or from 0.870 g/cc to 0.940 g/cc (1 cc=1 cm$^3$).

In one embodiment, each olefin-based polymer or polymer fraction, independently, comprises from 2 mole percent to 29 mole percent of an alpha-olefin, as determined by $^{13}$C NMR. Preferred alpha-olefins are discussed above.

In one embodiment, each olefin-based polymer or polymer fraction, independently, comprises from 5 mole percent to 9 mole percent of an alpha-olefin, as determined by $^{13}$C NMR. Preferred alpha-olefins are discussed above.

Olefin-based polymers include, but are not limited to, low density polyethylene (LDPE), high density polyethylene (HDPE), heterogeneously branched linear polymers (include Ziegler-Natta polymerized polymers, such as LLDPE, and include products such as DOWLEX Linear Low Density Polyethylene (LLDPE) available from The Dow Chemical Company), homogeneously branched substantially linear polymer (such as AFFINITY Polyolefin Plastomers and ENGAGE Polyolefin Elastomers, both available from The Dow Chemical Company) homogeneously branched linear polymers (such as EXACT Polymers available from ExxonMobil), and olefin multiblock copolymers (such as INFUSE Olefin Block Copolymers available from The Dow Chemical Company).

Olefin-based polymers also include polypropylene homopolymers, impact propylene based copolymers, and random propylene based copolymers.

An olefin-based polymer may comprise a combination of two or more embodiments as described herein.

An olefin-based polymer fraction may comprise a combination of two or more embodiments as described herein.

Definitions

Unless stated to the contrary, implicit from the context, or customary in the art, all parts and percents are based on weight, and all test methods are current as of the filing date of this disclosure.

The term "short chain branching," as used herein, refers to the side groups chemically bonded to a polymer backbone, created by copolymerization of ethylenically unsaturated monomers, such as, for example, propylene, butene, hexene, octene, and dodecene. Each short chain branch result from the incorporation of one such monomer into the polymer backbone.

The term "short chain branching distribution" and similar terms, as used herein, refer to the distribution of short chain branches within the polymer molecules of a polymer.

The term "polymer microstructure" and "microstructure" similar terms, as used herein, refer to the monomeric structures of the polymer molecules that make-up a polymer. Typically, microstructure refers to the amount and distribution of short chain branches, due to the incorporation of comonomer (for example, ethylenically unsaturated monomer) into the growing polymer chains of the polymer. The amount of comonomer incorporated typically influences the density of the final polymer. Thus, typically, polymers containing the same types of monomer and comonomer, but of different densities, have different polymer microstructures. Also, polymers prepared with different catalysts, typically have different polymer microstructures.

The term "peak height maximum" and similar terms, as used herein in reference to a chromatogram, refer to the elution time or retention volume at which a local maximum in the concentration signal (Intensity) is observed. Each local maximum typically designates a separate "peak" or a peak shoulder.

The term "olefin-based polymer fraction" and similar terms, as used herein, refer to a portion of a polymer that has a different polymer microstructure, and which typically has been prepared using a different catalyst and/or under different polymerization conditions; or a portion of a polymer that has been isolated from the bulk of the polymer.

The terms "HT-TGIC" and "TGIC," as used herein, refer to High Temperature Thermal Gradient Interaction Chromatogram (for example, see Cong, et al., Macromolecules, 11, 44 (8), 3062).

The term "CEF, as used herein, refer to Crystallization Elution Fractionation (for example, see Monrabal., et al., Macromol. Symp. 2007, 257, 71).

The term "TREF," as used herein, refer to Temperature Rising Elution Fractionation (for example, see Wild et al, *Journal of Polymer Science, Poly. Phys. Ed.*, Vol. 20, p. 441 (1982)).

The term "chromatogram" and similar terms, as used herein, refer to a profile generated during the separation of a polymer sample into polymer fractions, and showing an intensity (typically, an infrared absorbance corresponding to the concentration of polymer fraction) as a function of elution time or elution volume or elution temperature.

The term "fractionation and fractionating," as used herein, refers to separating components in a polymer sample according to their molecular properties, such as size and/or monomer content, or chemical composition.

The term "retention time" or "elution time," as used herein, refers to the time a polymer fraction elutes from a separation column or columns.

The term "retention volume or elution volume," as used herein, refers to the volume of eluent eluted from separation column(s). The volume=flow rate×elution time.

The term "stationary phase," as used herein, refers to a material which exists in the fluid stream as a solid form in a chromatographic process.

The term "solvent," as used herein, refers to a substance capable of dissolving another substance (solute).

The term "eluent," as used herein, refers to a solvent or a mixture of two or more solvents used in a chromatography process to move, or elute, one or more substances from a stationary support material.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities, for example, catalyst residues, may be incorporated into and/or within a polymer.

The term "interpolymer," as used herein, refers to polymers prepared by the polymerization of at least two different types of monomers. The generic term interpolymer includes copolymers (employed to refer to polymers prepared from two different monomers), and polymers prepared from more than two different types of monomers.

The term "olefin-based polymer," as used herein, refers to a polymer that comprises a majority amount of polymerized olefin monomer, for example ethylene or propylene, (based on weight of the polymer) and, optionally, at least one comonomer.

The term "ethylene-based polymer," as used herein, refers to a polymer that comprises a majority amount of polymerized ethylene monomer (based on weight of the polymer) and, optionally, at least one comonomer.

The term "ethylene-based interpolymer," as used herein, refers to an interpolymer that comprises a majority amount of polymerized ethylene monomer (based on weight of the interpolymer) and at least one comonomer.

The term "ethylene-based copolymer," as used herein, refers to a copolymer that comprises a majority amount of polymerized ethylene monomer (based on weight of the copolymer) and one comonomer, as the only two monomer types.

The term "ethylene/α-olefin interpolymer," as used herein, refers to an interpolymer that comprises a majority amount of polymerized ethylene monomer (based on the weight of the interpolymer) and at least one α-olefin.

The term, "ethylene/α-olefin copolymer," as used herein, refers to a copolymer that comprises a majority amount of polymerized ethylene monomer (based on the weight of the copolymer), and an α-olefin, as the only two monomer types.

The term, "polyethylene homopolymer," as used herein, refers to a polymer that comprises only polymerized ethylene monomer.

The term "propylene-based polymer," as used herein, refers to a polymer that comprises a majority amount of polymerized propylene monomer (based on weight of the polymer) and, optionally, at least one comonomer.

The term "propylene-based interpolymer," as used herein, refers to an interpolymer that comprises a majority amount of polymerized propylene monomer (based on weight of the interpolymer) and at least one comonomer.

The term "propylene-based copolymer," as used herein, refers to a copolymer that comprises a majority amount of polymerized propylene monomer (based on weight of the copolymer) and one comonomer, as the only two monomer types.

The term "propylene/α-olefin interpolymer," as used herein, refers to an interpolymer that comprises a majority amount of polymerized propylene monomer (based on the weight of the interpolymer) and at least one α-olefin.

The term, "propylene/α-olefin copolymer," as used herein, refers to a copolymer that comprises a majority amount of polymerized propylene monomer (based on the weight of the copolymer), and an α-olefin, as the only two monomer types.

The term "propylene/ethylene interpolymer," as used herein, refers to an interpolymer that comprises a majority amount of polymerized propylene monomer (based on the weight of the interpolymer) and at least ethylene.

The term, "propylene/ethylene copolymer," as used herein, refers to a copolymer that comprises a majority amount of polymerized propylene monomer (based on the weight of the copolymer), and ethylene, as the only two monomer types.

The term "composition," as used herein, includes a mixture of materials which comprise the composition, as well as reaction products and decomposition products formed from the materials of the composition.

The term "multidimensional chromatography," as used herein, refers to the coupling together of multiple separation mechanisms (for example, see J. C. Giddings (1990), Use of Multiple Dimensions in Analytical Separations, in Hernan Cortes Editor, *Multidimensional Chromatography: Techniques and Applications* (1st ed. pp. 1), New York, N.Y.: Marcel Dekker, Inc.).

The term, "cycle," as used herein, in reference to the temperature versus time profile, for a chromatographic method described herein, refers to an increase in the temperature of the stationary phase, followed by a decrease in the temperature of the stationary phase; here cycle=n'+1. No cycle for the comparative analysis (cycle=0).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Particle Size Distribution ($D_{50}$, $D_{10}$, $D_{90}$)

The particle size distribution is measured with an ACCUSTZFR 780 OPTICAL PARTICLE SIZER (Particle Size System, Florida, USA), and uses the principle of Single Particle Optical Sizing (SPOS) to count and size particles, one at a time, thus eliminating missed particles, and providing accurate particle size and count information. The illumination/detection system, in the sensor, is designed to provide a monotonic increase in pulse height with increasing particle diameter. The standard calibration curve is obtained by measuring a series of standard polystyrene latex samples from NIST Traceable Monodisperse Standards (Duke). The detailed procedure for calibration can be found in the operation manual provided by Particle Size System. A particle size distribution (PSD) is constructed by counting a large amount of particles (at least 55,000 particles). The sample (particles) is suspended in methanol (HPLC grade; other suitable solvents include mineral oil or silicon oil), at low enough concentration, to avoid coincidence counting (two particles in sensoring zone), according to the operation procedure provided by Particle Size System.

The $D_{50}$, $D_{10}$ and $D_{90}$, each on a volume basis, are calculated by the software of ACCUSIZER 780. Other solvents suitable include TCB (HPLC grade) and ODCB (HPLC grade). The median diameter ($D_{50}$, typically in micron), is defined as the particle diameter where half of the mass distribution (volume distribution) resides above this point, and half resides below this point. The $D_{10}$ is defined as the particle diameter where 10% of the mass lies below this point ($D_{10}$). The $D_{90}$ is defined as the particle diameter that 90 percent of the mass lies below this point ($D_{90}$).

Density

Samples are prepared according to ASTM D 1928. Measurements are made within one hour of sample pressing using ASTM D792, Method B.

Melt Index

Melt index, MI, I2 or $I_2$, is measured in accordance with ASTM D 1238, Condition 190° C./2.16 kg, and is reported in grams eluted per 10 minutes. The "I10 or $I_{10}$" melt index is measured in accordance with ASTM D 1238, Condition 190° C./10 kg, and is reported in grams eluted per 10 minutes. For propylene-based polymers, the melt flow rate (MFR) is measured in accordance with ASTM D-1238, condition 230° C./2.16 kg.

Gel Permeation Chromatography

The chromatographic system consists of either a Polymer Laboratories Model PL-210 (Agilent) or a Polymer Laboratories Model PL-220 (Agilent) or PolymerChar HT GPC (Spain). The column and carousel compartments are operated at 140° C. Three Polymer Laboratories, 10-μm Mixed-B columns are used with a solvent of 1,2,4-trichlorobenzene. The samples are prepared at a concentration of "0.1 g of polymer" in "50 mL of solvent" or "16 mg of polymer in 8 mL of solvent." The solvent used to prepare the samples contain 200 ppm of BHT. Samples are prepared by agitating lightly for four hours, at 160° C. The injection volume used is "100 microliters," and the flow rate is "1.0 mL/min." Calibration of the GPC column set is performed with twenty one narrow molecular weight distribution polystyrene standards purchased from Polymer Laboratories. The molecular weight (MW) of the standards ranges from 580 to 8,400,000 g/mol, and the standards are contained in six "cocktail" mixtures. Each standard mixture has at least a decade of separation between individual molecular weights. The standards are purchased from Polymer Laboratories (Shropshire, UK). The polystyrene standards are prepared at "0.001 g in 20 mL of solvent" for molecular weights equal to, or greater than, 1,000,000 g/mol, and at "0.005 g in 20 mL of solvent" for molecular weights less than 1,000,000 g/mol.

The polystyrene standard peak molecular weights are converted to polyethylene molecular weights using Equation 1:

$$M\text{polyethylene}=A(M\text{polystyrene})^B \quad \text{(Eq. 1)},$$

where M is the molecular weight, A has a value of 0.4316 and B is equal to 1.0 (T. Williams and I. M. Ward, *Polym. Letters*, 6, 621-624 (1968)). A third order polynomial is determined to build the logarithmic molecular weight calibration as a function of elution volume. Polyethylene equivalent molecular weight calculations are performed using VISCOTEK TriSEC software Version 3.0 for Agilent GPC instrument or GPCOne software for PolymerChar GPC instrument.

High Temperature Thermal Gradient Interaction Chromatography

HT-TGIC (or TGIC) measurement uses a commercial Crystallization Elution Fractionation instrument (CEF) (Polymer Char, Spain) to perform high temperature thermal gradient interaction chromatography (HT-TGIC, or TGIC) measurement (Cong, et al., Macromolecules, 2011, 44 (8), 3062-3072). The CEF instrument is equipped with an IR-5 detector (such as that sold commercially from PolymerChar, Spain), two-capillary viscometer (PolymerChar, Spain) and a two angle light scattering detector Model 2040 (such as those sold commercially from Agilent). Ortho-dichlorobenzene (ODCB, 99% anhydrous grade) and Silica gel 40 (particle size 0.2-0.5 mm) (such as commercially available from EMD Chemicals) are obtained. The silica gel is dried in a vacuum oven at 160° C. for at least two hours before use. The ODCB is sparged with dried nitrogen ($N_2$) for one hour before use. Dried nitrogen is obtained by passing nitrogen at <90 psig over dried $CaCO_3$ and 5 Å molecular sieves. The ODCB is further dried by adding five grams of the dried silica to two liters of ODCB, or by pumping the ODCB through a column or columns packed with dried silica, at 0.1 mL/min to 2.0 ml/min. Dried ODCB was hereinafter referred to as "ODCB-m." Otherwise stated, a sample solution is prepared, using the autosampler, by dissolving a polymer sample in ODCB-m, at 4 mg/mL (32 mg of sample in 8 mL of ODCB-m), under shaking at 160° C. for 120 min. The TGIC data was processed on a PolymerChar (Spain) "GPC One" software platform. The raw chromatogram was obtained by exporting with GPCOne software. Stationary phase: a) high porosity: HYPERCARB™ 7 um column (from Thermofish Scientific); b) low porosity graphite (from Superior Graphite Co. (USA)) with characteristics listed in Table 6 (see the experimental section). The detailed experimental conditions are listed in Table 1 and Table 4.

Column Preparation—Low Porosity Stationary Phase
Hardware for Packing Columns—HT-TGIC Stainless steel column, frit, end fitting of the column were obtained from Agilent Technologies (previously Polymer-Lab Inc.). An Agilent Model 1100 Liquid Chromatography Pump was used for the slurry packing method. TCB (1,2, 4-trichlorobenzene) was the slurry medium. A slurry packing reservoir was constructed of "0.46 cm" internal diameter stainless steel tubing with Valco end fittings. The reservoir was 100 mm in length. A standard ¼" outside diameter tube union was used to connect the packing reservoir to the empty analytical column.

Methodologies for Packing Columns

1. Packed columns that exhibit good mass transfer properties, including low back pressure at standard operating conditions of flow and temperature, low sensitivity to shock from abruptly changing conditions, and lack of channels and void spaces.
2. Packed columns that have sufficient internal liquid volume to permit the studies of the effect of dynamic cooling on component resolution. The dynamic cooling is a process of using a slow flow during the cooling process of CEF and HT-TGIC (Monrabal et al, *Macromol. Symp.* 257, 71-79 (2007), and Cong, et al., Macromolecules, 11, 44 (8), 3062)).

The methodologies of preparing low porosity column(s) first uses (1) dry packing by using the tap-and-fill method, in which the added material is settled by tapping the column, or using an electric vibrating tool, followed by (2) slurry packing method, which uses a suspension or slurry of the substrate where the slurry is pumped into the column under flowing conditions (Striegel, Yau, et al., *Modern Size Exclusion Liquid Chromatography*, Wiley, the 2$^{nd}$ edition, Chapter 6).

For the simple tap-and-fill method, the column is suspended vertically. Substrate is added in small increments through a funnel, while the column being tapped or vibrated to settle the substrate. When the substrate is level with the end of the column, the end fitting is added, and the column is tightened. It is a standard practice to condition the columns prior to use, and to inspect the bed for settling or voids. If voids are found, more packing is added to level the end of the column.

For the slurry packing method, the substrate materials were dry added to the empty column. The reservoir and column with end fitting is then assembled, and connected to the Agilent pump. TCB is pumped upward, at a flow of 1 mL/min, through the reservoir, until air is displaced from the column. The flow is momentarily stopped, the column and reservoir is then inverted to a down-flow position. TCB is pumped at 3-5 mL/min through the column for at least twenty minutes, or until the system pressure reaches 2500 PSIG. The column is disconnected from the packing reservoir, and any excess packing at the end of the column is removed with a flat blade scraper to provide an even level with the end of the tubing. The end fitting is tightened into place, and the column is ready for conditioning.

Column Conditioning

The newly packed column is installed in the HT-TGIC instrument, and flow is established at 0.1 mL/min at room temperature. Depending on the material and how efficiently it is packed, the back pressure at this point is usually 2-10 Bar. The flow is increased in steps of 0.1 mL/min, allowing the pressure to stabilize between each increase, up to either 0.7 or 1.0 mL/min. The column temperature is increased to 60° C., and then a linear temperature ramp is used to heat the column, under flow, to 140° C. at 10° C./min. This final temperature is held for 20 minutes, and then the column is cooled at 10° C./min to 100° C., and pronounced ready for testing.

Mercury Porosimetry for Pore Size Distribution and Porosity

Pore size distribution was obtained by mercury porosimetry. The mercury porosimetry analysis was performed on a Micromeritics Autopore IV 9520, available from Micromeritics The samples were dried at 110° C., for 2 hours, and then mechanically out-gassed, while under vacuum, prior to analysis, to remove any physically adsorbed species (i.e., moisture) from the surface of the sample.

Test conditions included a Hg fill pressure of 0.50 psia, Hg contact angle of 130°, Hg surface tension of 485 dyn/cm, Hg density 13.53 g/mL, 30 minutes of evacuation time, large bore penetrometer (powder type: 1.131 stem volume) with 5-cc bulb, 30 seconds of equilibration time, 92-point pressure table (75 intrusion plus 17 extrusion pressure points), and mechanical evacuation <50-µm Hg. The low to high pressure cross over point was collected at approximately 39 psia (4.6 um). The pressure table used was generated to allow an even incremental distribution of pressures, on a log scale, from 0.5 to 60,000 psia, and was used for detecting pore size from 0.003-400-µm diameter. Mercury was forced into smaller and smaller pores as pressure was increased incrementally, from a vacuum, to a maximum of nearly 60,000 psia. To verify that the instrument was working properly, a Silica-Alumina reference material (Micromeritics lot A-501-46) was analyzed. The reported median pore diameter (volume) of the reference sample was 0.0072±0.0005 µm. The Autopore reported the median pore diameter (volume) of the reference material as 0.0071-µm.

Porosity was calculated by excluding the inter particle intrusion using the data processing software equipped with Micromeritics Autopore IV 9520. Skeletal density was computed after the volume of all pores larger than about 0.003 µm has been excluded from the volume presumed occupied by the material.

Nitrogen Adsorption/Desorption (B.E.T.)

Nitrogen adsorption/desorption analysis was performed on a Micromeritics Accelerated Surface Area & Porosimetry instrument (ASAP 2405), The samples were out-gassed at 200° C. for approximately 24 hours, while under vacuum, prior to analysis. Approximately 0.5 gram of the "as-received" sample was used for the analysis.

Typically, B.E.T. surface areas are achieved with a precision of <3% RSD (relative standard deviation). The instrument employs a static (volumetric) method of dosing samples, and measures the quantity of gas (nitrogen) that can be physically adsorbed on a solid at liquid nitrogen temperature. For the multi-point B.E.T. measurement, the volume of nitrogen uptake was measured at pre-selected relative pressure points, at constant temperature. The relative pressure was the ratio of the applied nitrogen pressure to the vapor pressure of nitrogen at the analysis temperature of 77 K. Pore sizes from about 17 to 3,000 Angstroms diameter are detected by this method.

Test conditions for the nitrogen adsorption/desorption isotherms include a 15 second equilibration interval, a 97-point pressure table (40 adsorption points, 40 desorption points, multi-point B.E.T. surface area, 20 micropore points, and 1-point total pore volume), a 5%/5 mmHg P/Po tolerance, and a 120 min Po interval. The porosity (%) is the ratio of the volume of the pores into which mercury can penetrate, at the pressure applied, to the total volume occupied by the given amount of the solid.

BET calculation was performed using the data processing software equipped from Micromeritics Accelerated Surface Area & Porosimetry instrument (ASAP 2405).

TLVSP Measurement

The separation column filled with solvent (TCB) is weighed at room temperature (w1, g). Next, the packing is emptied from the column, and dried under vacuum to a constant weight (w2, g). The empty column is dried and weighed (w3, g). The TLVSP (measured)=(w1-w2-w3)/(density of solvent), where the density of TCB is 1.454 g/mL at 25° C.

EXPERIMENTAL

The schematic drawing of the chromatography set up for each analysis is shown in FIG. 1.

Temperature Profiles

For each analysis a polymer solution is prepared by dissolving a polymer sample in at least one solvent, and at least part of polymer solution was injected onto on a stationary phase, and a temperature profile was run. Temperature in temperature profile stands for the temperature (° C.) of a forced air convection oven, where the stationary phase, within at least one column, is located.

Figure 2A:
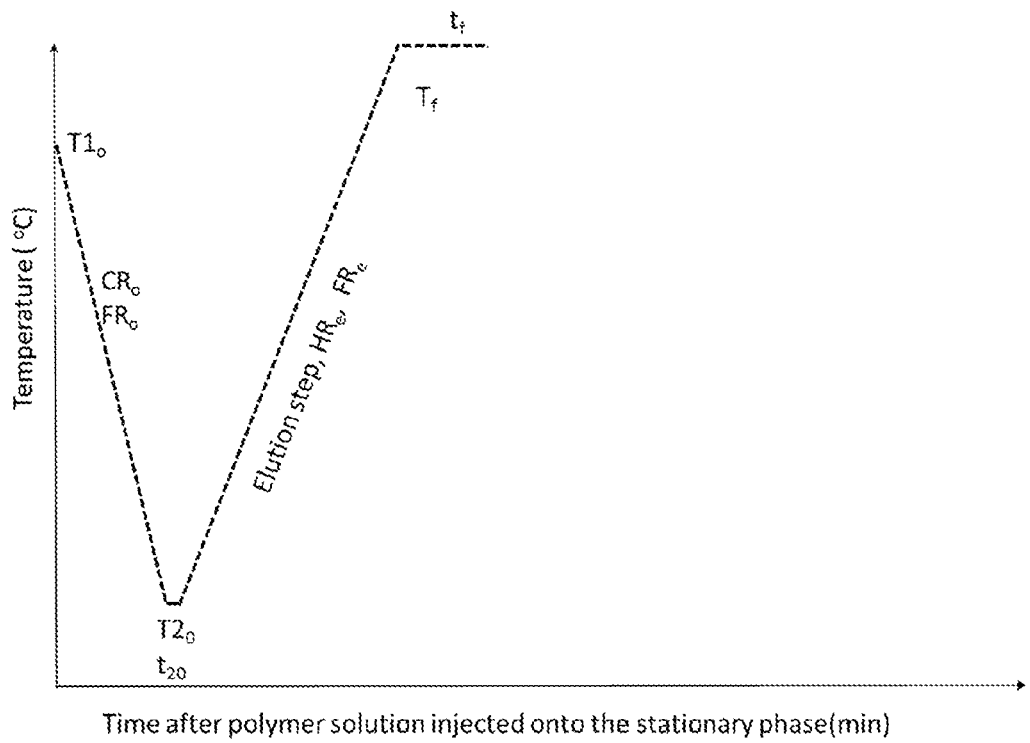
FIG. 2a depicts a schematic temperature versus time profile (after sample injected onto the column) for a comparative analysis.

The temperature profile for a comparative analysis has the following steps (see, for example, FIG. 2*a*):

1) Cooling step from $T1_0$ to $T2_0$ at a cooling rate of $CR_0$ and a flow rate of $FR_0$;

2) Once the temperature reached $T2_0$, the temperature is optionally held at $T2_0$ for a time period of $t_{20}$;

3) Elution step from $T2_0$ to $T_f$ at a Heating Rate ($HR_e$) and Flow rate ($FR_e$), and where $T_f$ is equal or higher than $T1_0$; and eluting the polymer sample from the stationary phase during this temperature increase; and when the stationary phase reaches temperature $T_f$, optionally maintaining the temperature at $T_f$ for a time $t_f$; and generating a comparative chromatogram (for example, intensity versus elution temperature or intensity versus elution time).

Figure 2B:
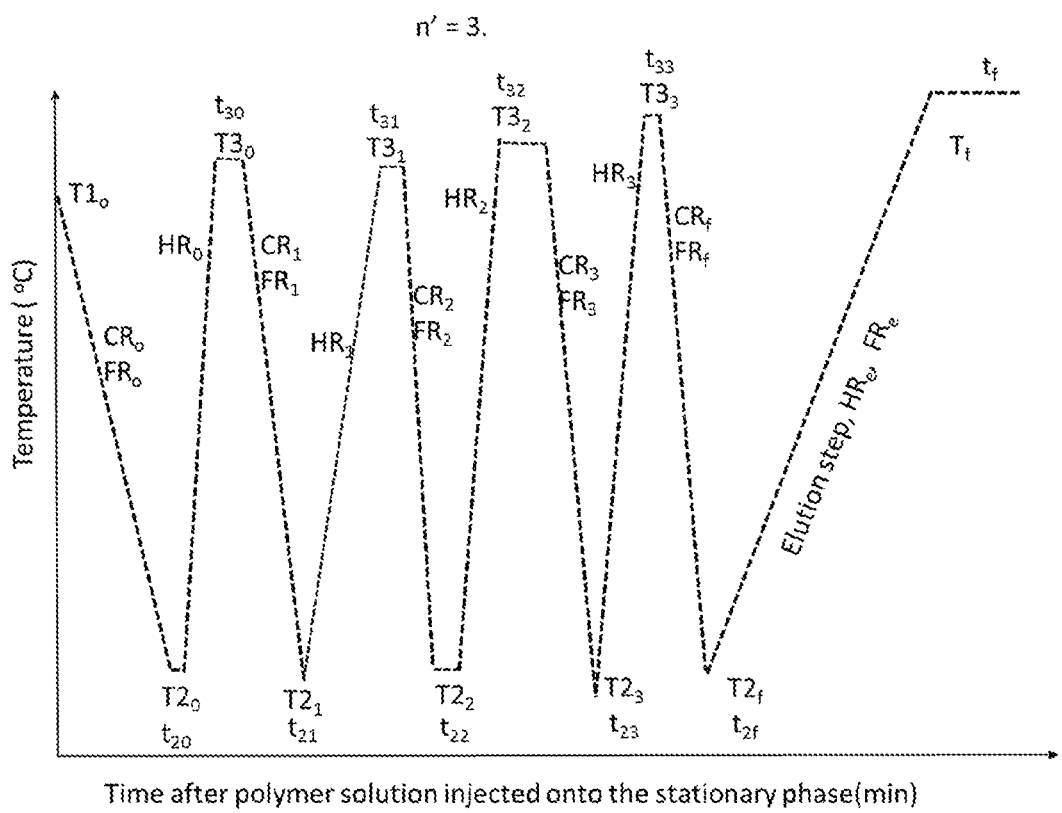
FIG. 2b depicts a schematic temperature versus the time profile (after sample injected onto the stationary phase) for an inventive analysis.

The temperature profile for an inventive analysis has the following steps (see, for example, FIG. 2*b*):

1) Cooling step from $T1_0$ to $T2_0$ at a cooling rate of $CR_0$ and a flow rate of $FR_0$;

2) Once the temperature reached $T2_0$, the temperature is optionally held at $T2_0$ for a time period of $t_{20}$;

3) Heating up from $T2_0$ to $T3_0$ at a heating rate of $HR_0$, while the flow rate remains at zero mL/min;

4) Once the temperature reaches $T3_0$, the temperature is held at $T3_0$ for a time period of $t_{30}$;

Steps 5) and 6) below, can be repeated; and wherein at each n value, the eluent flow rate of step 6) is $FR_n$; and wherein at least one $T3_n$ (for n from 1 to n', where n'≥1) is greater than $T1_0$;

5) Setting a constant eluent flow rate ($FR_n$) through the stationary phase, while simultaneously cooling the stationary phase at a cooling rate $CR_n$, preferably selected from 0.1° C./min to 15.0° C./min, to a minimum temperature $T2_n$, where $T2_n<T3_{n-1}$; and wherein the flow of the eluent through the stationary phase is stopped at temperature $T2_n$;

6) When the temperature reaches $T2_n$, optionally maintaining the temperature at the stationary phase for a time $t_{2n}$; increasing the temperature of the stationary phase to $T3_n$, at a heating rate $HR_n$, preferably selected from 1.0° C./min to 100° C./min, where $T3_n>T2_n$, while maintaining no flow of eluent through the stationary phase; and when the temperature of the stationary phase reaches temperature $T3_n$, maintaining no flow rate through the stationary phase for an additional $t_{3n}$, preferably from 1.0 to 10.0 minutes; and maintaining the temperature of the stationary phase at $T3_n$ for a time $t_{3n}$;

7) Cooling, at a rate $CR_f$, the stationary phase to a temperature $T2_f$, and when the temperature reaches temperature $T2_f$, optionally maintaining the temperature at $T2_f$ for a time $t_{2f}$;

8) increasing the flow rate of the eluent through the stationary phase to at least 0.1 ml/min, while increasing the temperature of the stationary phase to $T_f$ ($T_f>T2_f$ and $T_f≥T1_0$), and eluting the polymer sample from the stationary phase during this temperature increase; and when the stationary phase reaches temperature $T_f$, and optionally maintaining the temperature at $T_f$ for a time $t_f$; and generating a chromatogram (for example, intensity versus elution temperature or intensity versus elution time).

Preferably, the number of cycles can be increase from 1 to 10, or more than 10. Preferably, the total cooling flow during all of the cooling steps does not exceed TLVSP (for example, from Equation (B)); and at least one of $T3_n$ is greater than, or equal to, $T1_0$.

The value of TLVSP can be increased, allowing more cycles, by connecting additional packed columns containing additional stationary phase, in series with the first column, and before the detector.

Representative Determination of Resolution Index (RI)

The polymer sample has two individual polymer components with different microstructures. In this case, the two individual components are not baseline separated in HT-TGIC chromatogram.

Figure 3:
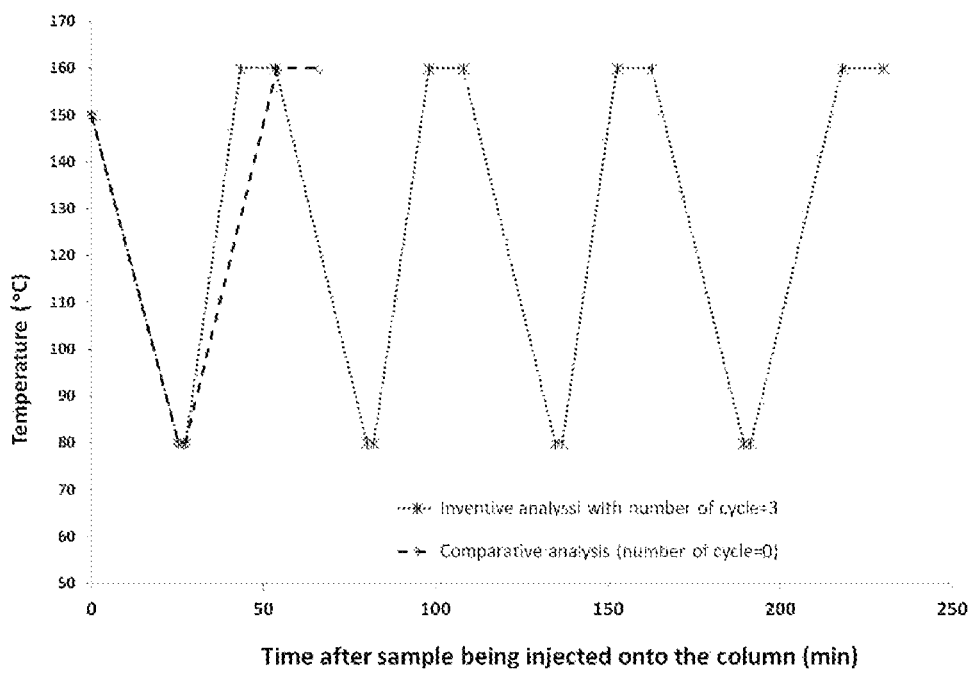
FIG. 3 depicts the temperature versus the time profiles (after sample injected onto the column) of the cooling, heating and elution steps for an inventive analysis (dotted line—several cycles) and a comparative analysis (dashed line) for Sample #1 and Sample #2.
Figure 4:
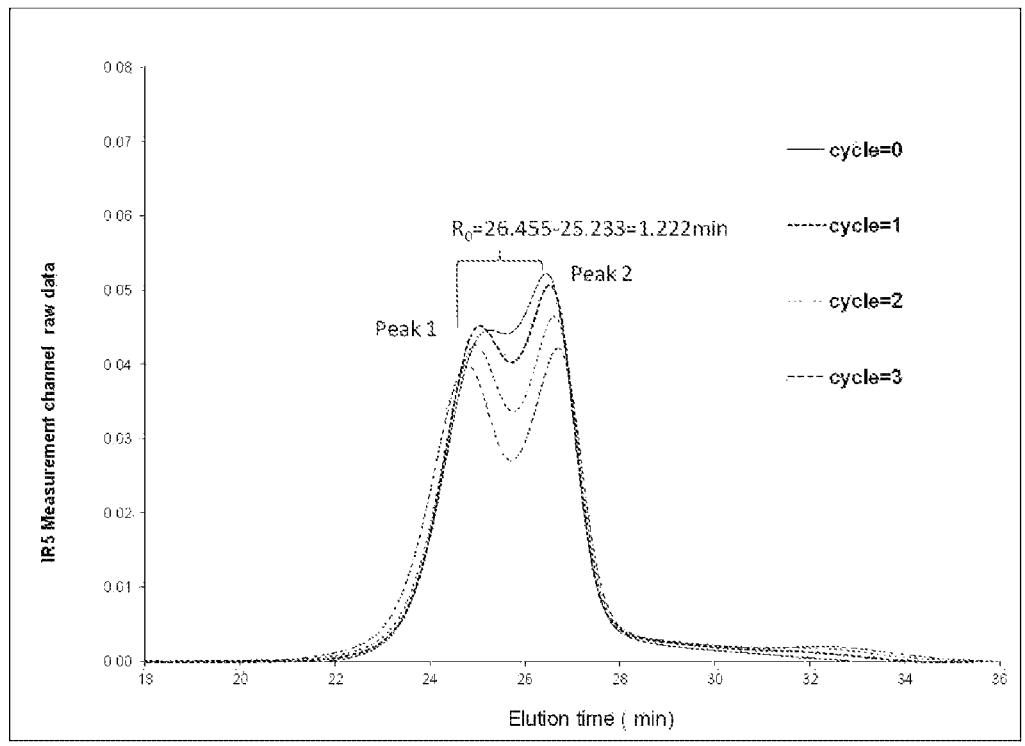
FIG. 4 depicts the raw HT-TGIC chromatograms of the Sample #1 (direct output of IR-5 detector measurement channel (absorbance) versus elution time (min)).

The sample is analyzed by the comparative method (no cycle, or cylcle=0) and the inventive method (cycle=1, 2; where the total number of cycles=n'+1) according to the temperature profiles in FIG. 3. The raw chromatogram (IR-5 measurement channel versus elution time (ET, min) is obtained (see FIG. 4; here cycle=0 (comparative), cycle=1 (n'=0), cycle=2 (n'=1), cycle=3 (n'=2)).

The difference in elution time of the peaks of the sample is calculated when cycle=0: Ro (min)=ΔET=ET(peak2)−ET (peak1).

The difference in elution time at the peak of each HT-TGIC chromatogram obtained by using the inventive analysis (cycle≥1) is calculated as follows: Rc (min)=ΔET (cycle≥1)=ET(peak2)−ET (peak1).

For each chromatogram, the Resolution Index (RI) is calculated as follows: (RI)=((RC−R0)/R0)×100.

Polymers

Three ethylene octene random copolymers made by single site catalyst with a narrow SCBD (mono-mode excluding less than 2% of soluble fraction) were used.

Ethylene octene random copolymer A (EO-A) with a density 0.9239 g/cc, Mw of 102,900 g/mole, Mw/Mn of 2.2, I2 of 1.0 g/10 minutes, I10/I2 of 6.4.

Ethylene octene random copolymer B (EO-B) with a density 0.9520 g/cc, Mw of 37,500 g/mole, Mw/Mn of 2.0, I2 of 63.0 g/10 minutes).

Ethylene octene random copolymer B (EO-C) with a density 0.9567 g/cc, Mw of 104,000 g/mole, Mw/Mn of 2.0, I2 of 1.0 g/10 minutes and I10/I2 of 6.7).

Study 1

Sample #1 was made by weighing equal amounts of ethylene octene random copolymer EO-A and ethylene octene random copolymer EO-B to give a final concentration of polymer in solution of 4.0 mg/mL. Sample #1 was analyzed by HT-TGIC (see test method section and Table 1) using a comparative analysis (the number of cycle=0) and an inventive analysis (the number of cycle=n'+1=3). The stationary phase was low porosity graphite (Superior Graphite Co., USA) with characteristics listed in Table 6 below.

The detailed experimental parameters are listed in Table 1. The schematic drawing of the temperature profile of the cooling, heating and eluting steps is shown in FIG. 3. Table 1 shows the Resolution Index (RI) at different number of the cycles. For the comparative analysis (cycle=0), the RI values was 0. For the inventive analysis, for the number of cycles was 1, 2 and 3, the RI was 23%, 31% and 57%, respectively for each cycle. This indicates that with the increase in the number of cycles, there is a significant increase in the resolution of the respective chromatogram. In addition, the improvement in separation can be clearly observed from HT-TGIC chromatograms (see FIG. 4). Here, the measured TLVSP of the packed column is 3.5 ml.

The equations for TLVSP are met. $TLVSP_{calc}$ (n'=2)=0.03 ml/min*[(150° C.−80° C.)/3° C./min]+0.03 ml/min*[(160° C.−80° C.)/3° C./min]+0.03 ml/min*[(160° C.−80° C.)/3° C./min]+0.03 ml/min*[(160° C.−80° C.)/3° C./min]=3.1 mL, which is <3.5 mL (measured). See Table 1 below. Thus, for n=1, calculated TLVSP=2.3; for n=0, calculated TLVSP=1.5 ml.

TABLE 1

HT-TGIC experimental parameters for Sample#1 with low porosity stationary phase. The Total Liquid Volume of Stationary Phase measured is 3.5 ml. Two columns, 0.46(ID) × 25 (length) cm column dimension.

Comparative analysis with number of cycles = 0.
Injection loop size = 200 ul.

| | |
|---|---|
| $T1_o$ | 150° C. |
| $T2_0$ | 80° C. |
| $t_{2_0}$ | 2 min |
| $FR_0$ | 0.03 mL/min |
| $CR_0$ | 3° C./min |
| Tf | 160° C. |
| $t_f$ | 10 min |
| $FR_e$ | 0.5 mL/min |
| $HR_e$ | 3° C./min |

Inventive analysis with the number of cycles = 3.
Injection loop size = 200 ul

| | |
|---|---|
| $T1_o$ | 150° C. |
| $T2_0$ | 80° C. |
| $t_{2_0}$ | 2 min |
| $FR_0$ | 0.03 mL/min |
| $CR_0$ | 3° C./min |
| $T3_0 = T3_1 = T3_2$ | 160° C. |
| $t_{3_0} = t_{3_1} = t_{3_2}$ | 10 min |
| $T2_1 = T2_2 = T2_3$ | 80° C. |
| $t_{2_1} = t_{2_2} = t_{2_3}$ | 2 min |
| $FR_1 = FR_2 = FR_3$ | 0.03 mL/min |
| $CR_1 = CR_2 = CR_3$ | 3° C./min |
| $HR_0 = HR_1 = HR_2$ | 5° C./min |
| Tf | 160° C. |
| $t_f$ | 10 min |
| $FR_e$ | 0.5 mL/min |
| $HR_e$ | 3° C./min |

TABLE 2

Resolution Index (RI) of Sample #1 for the comparative analysis (cycle = 0) and the inventive analysis (cycle = 1, 2 and 3); ET = Elution Time

| Sample# 1 | Elution time for Peak 1 (min) | Elution time for Peak2 (min) | ΔET (min) | RI | Total analysis time (after polymer solution injected onto the substrate support) (min) |
|---|---|---|---|---|---|
| cycle = 0 | 25.233 | 26.455 | 1.222 (R0) | 0% | 66 |
| cycle = 1 | 25.014 | 26.554 | 1.540 (RC) | 26% | 120.6 |

TABLE 2-continued

Resolution Index (RI) of Sample #1 for the comparative analysis (cycle = 0) and the inventive analysis (cycle = 1, 2 and 3); ET = Elution Time

| Sample# 1 | Elution time for Peak 1 (min) | Elution time for Peak2 (min) | ΔET (min) | RI | Total analysis time (after polymer solution injected onto the substrate support) (min) |
|---|---|---|---|---|---|
| cycle = 2 | 24.95 | 26.552 | 1.602 (RC) | 31% | 175.3 |
| cycle = 3 | 24.794 | 26.707 | 1.913 (RC) | 57% | 230 |

Study 2

Sample #2 is made by weighing equal amounts of ethylene octene random copolymer EO-A and ethylene octene random copolymer EO-C to give a final concentration of polymer in solution of 4.0 mg/mL. Sample #2 is analyzed for HT-TGIC (see test method section, and Table 1) with the comparative analysis (no cycles) and inventive analysis (the total number of cycle=n'+1=3). The stationary phase was low porosity graphite from Superior Graphite Co. (USA) with characteristics listed in Table 6 below.

Figure 5:
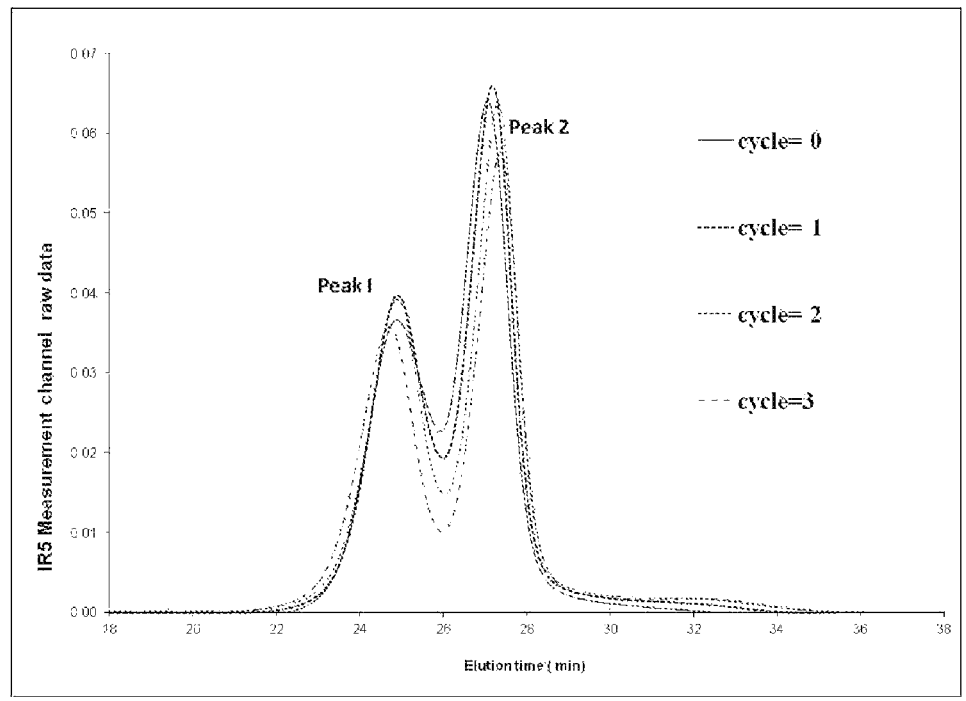
FIG. 5 depicts the raw HT-TGIC chromatograms of the Sample #2 (direct output of IR-5 detector measurement channel (absorbance) versus elution time (min)).

The detailed experimental parameters are listed in Table 1 and shown in FIG. 3. Table 3 shows the Resolution Index (RI) at different numbers of cycles. When the number of cycles is 1, 2 and 3, RI is 7%, 14% and 26%, respectively. This indicates that with the increase in the number of cycles, there is a significant increase in the resolution of the respective chromatogram. In addition, as shown in FIG. 5, the peak valley between the Peak 1 and Peak 2 gets deeper when the number of the cycles increases, indicating the separation gets better with the number of cycles.

Equations for TLVSP are met: $TLVSP_{calc}$ (n'=2)=0.03 ml/min*[(150° C.−80° C.)/3° C./min]+0.03 ml/min*[(160° C.−80° C.)/3° C./min]+0.03 ml/min*[(160° C.−80° C.)/3° C./min]=3.1 mL, which is <3.5 ml (measured). See Table 1 above (same heating rates, cooling rates, flow rates, temperature profies as in Table 1). Thus, for n=1, calculated TLVSP=2.3 ml; n=0, calculated TLVSP=1.5 ml.

TABLE 3

Resolution Index (RI) demonstrated by Sample#2 for the comparative analysis (cycles = 0) and the inventive analysis (cycle = 1, 2 and 3) with low porosity stationary phase

| Sample# 2 | Elution time for Peak 1 (min) | Elution time for Peak2 (min) | ΔET (min) | RI | Total analysis time (after polymer solution injected onto the substrate support) (min) |
|---|---|---|---|---|---|
| cycle = 0 | 24.929 | 27.055 | 2.126 (R0) | 0% | 66 |
| cycle = 1 | 24.929 | 27.195 | 2.266 (RC) | 7% | 120.6 |
| cycle = 2 | 24.929 | 27.343 | 2.414 (RC) | 14% | 175.3 |
| cycle = 3 | 24.714 | 27.395 | 2.681 (RC) | 26% | 230 |

Study 3

Figure 6:
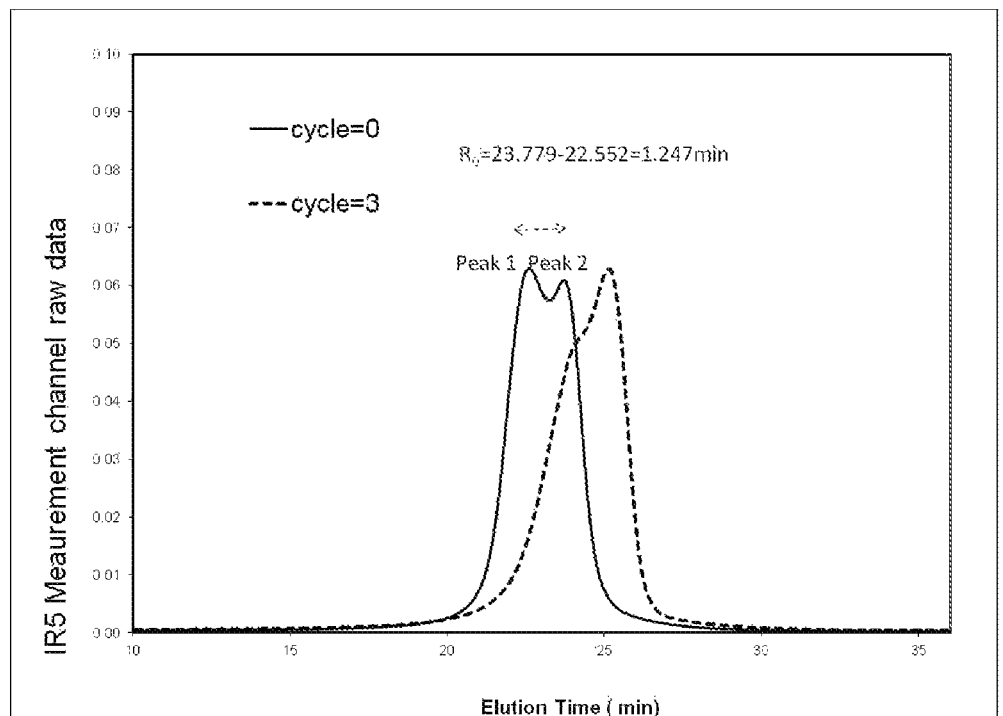
FIG. 6 depicts the HT-TGIC raw chromatogram of Sample #1, measured using high porosity graphite stationary phase, at number of cycles being zero and three.

Highly porous graphite (HYPERCARB column) is commonly used as the stationary phase in HT-TGIC (see, for example, Cong, et al., Macromolecules, 2011, 44 (8), pp 3062-3072). See Table 6 below. The HYPERCARB column is used to analyze the samples, Sample #1 and Sample #2. The detailed experimental conditions are listed in Table 4. FIG. 6 shows the comparison of the HT-TGIC raw chromatograms of Sample #1 with the total number of cycles being zero and 3, respectively. Surprisingly, the EO-A and EO-B is separated much better when the number of cycle being zero than the result obtained by the number of cycles at 3 (n'=2). In other word, the separation of EO-A and EO-B worsen with the increase in the number of cycles, when using highly porous stationary phase HYPERCARB. This result is very different from the inventive analysis where the separation of Sample #1 increases with the number of cycles. As shown in Table 5, the RI value is zero for cycle=0, while for number of cycle=3, the RI actually reduced to −13%. The detailed experimental parameters are shown in Table 4. The highly porous graphite has a substantial size exclusion effect (see Cong & Parrott et al., "Method and apparatus for size exclusion chromatography of polymers", WO 2012166861A1), thus confounding HT-TGIC separation with multiple cycles.

TABLE 4

HT-TGIC experimental parameters for Sample#1 and Sample #2 using zero cycle and three cycles with two highly porous HYPERCARB columns (Col. dimension: 5 microns 100 × 0.46 mm)

The number of cycle = 0.
Injection loop size = 200 ul.

| | |
|---|---|
| $T1_0$ | 150° C. |
| $T2_0$ | 80° C. |
| $t_{2_0}$ | 2 min |
| $FR_0$ | 0.01 mL/min |
| $CR_0$ | 3° C./min |
| Tf | 160° C. |
| $t_f$ | 10 min |
| $FR_e$ | 0.5 mL/min |
| $HR_e$ | 3° C./min |

The number of cycles = 3.
Injection loop size = 200 ul.

| | |
|---|---|
| $T1_0$ | 150° C. |
| $T2_0$ | 80° C. (hold for 2 minutes after the temperature of stationary phase reaches at T2) |
| $t_{2_0}$ | 2 min |
| $FR_0$ | 0.01 mL/min |
| $CR_0$ | 3° C./min |
| $HR_0 = HR_1 = HR_3$ | 5° C./min |
| $T3_0 = T3_1 = T3_2$ | 160° C. |
| $t_{3_0} = t_{3_1} = t_{3_2}$ | 10 min |
| $T2_1 = T2_2 = T2_f$ | 80° C. |
| $t_{2_1} = t_{2_2} = t_{2_f}$ | 2 min |
| $FR_1 = FR_2 = FR_3$ | 0.01 mL/min |
| $CR_1 = CR_2 = CR_3$ | 3° C./min |
| $T_f$ | 160° C. |
| $t_f$ | 10 min |
| $FR_e$ | 0.5 mL/min |
| $HR_e$ | 3° C./min |

TABLE 5

Resolution Index (RI) of Sample #1 and Sample #2 with HYPERCHAR Column

| Sample# 1 | Elution time for Peak 1 (min) | Elution time for Peak2 (min) | ΔET (min) | RI |
|---|---|---|---|---|
| cycle = 0 | 22.532 | 23.779 | 1.247 (R0) | 0 |
| cycle = 3 | 24.043 | 25.127 | 1.084 (RC) | −13.1% |

| Sample# 2 | Elution time for Peak 1 (min) | Elution time for Peak2 (min) | ΔET (min) | |
|---|---|---|---|---|
| cycle = 0 | 22.501 | 24.232 | 1.731 (R0) | 0 |
| cycle = 3 | 23.968 | 25.687 | 1.719 (RC) | −0.7% |

Figure 7:
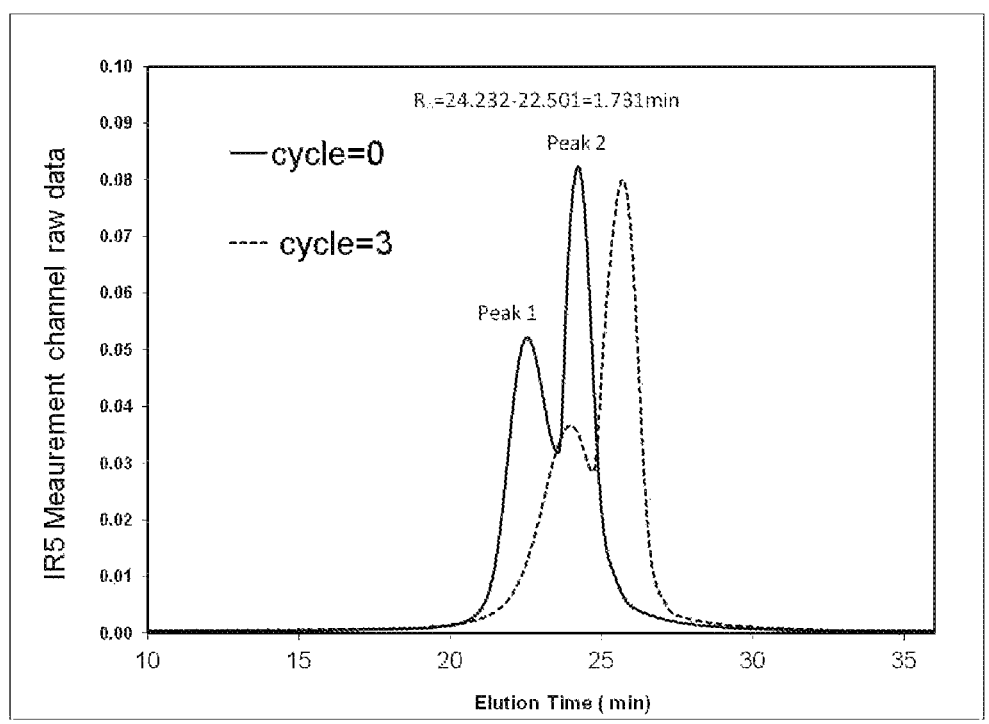
FIG. 7 depicts the HT-TGIC raw chromatogram of Sample #2, measured using high porosity graphite stationary phase, at number of cycles being zero and three.

FIG. 7 shows the comparison of HT-TGIC raw chromatograms of Sample #2 with the number of cycles being zero and three, respectively, and obtained with HYPERCARB column. The EO-A and EO-C are separated better, when the number of cycles is zero, than when the number of cycles is three. In other words, the separation of EO-A and EO-C worsen with the increase in the number of cycles, when a highly porous graphite as stationary phase. This result is very different from the inventive analysis where the separation of Sample #1 (FIG. 4 and Table 2) and Sample #2 (FIG. 5 and Table 3) increases with the number of cycles. The lower porosity of the stationary phase helps to improve in HT-TGIC resolution. As shown in Table 5, RI value is zero for cycle=0, while for number of cycle=3 RI actually reduced to −0.7%.

In the determination of the chemical composition distribution analysis (CCD) or short chain branching analysis (SCBD) by HT-TGIC, co-elution (also, commonly named as co-adsorption) refers to the phenomenon that polyolefin chains with similar, but different, microstructures elute together, leading to errors in the reported CCD) (Alghyamah et al., Macromol. Chem. Phys. 2015, 216, 38-48), Co-elution in HT-TGIC also poses a great challenge to model the CCD, especially for polymers with complex microstructures. With a polymer sample, co-elution can be observed by comparing the mathematically calculated CCD (and/or HT-TGIC chromatogram) from individual polymer components with the experimentally measured CCD (or HT-TGIC chromatogram). In the presence of co-elution, the experimentally measured CCD does not overlay well with the expected CCD for the sample.

Figure 8A:
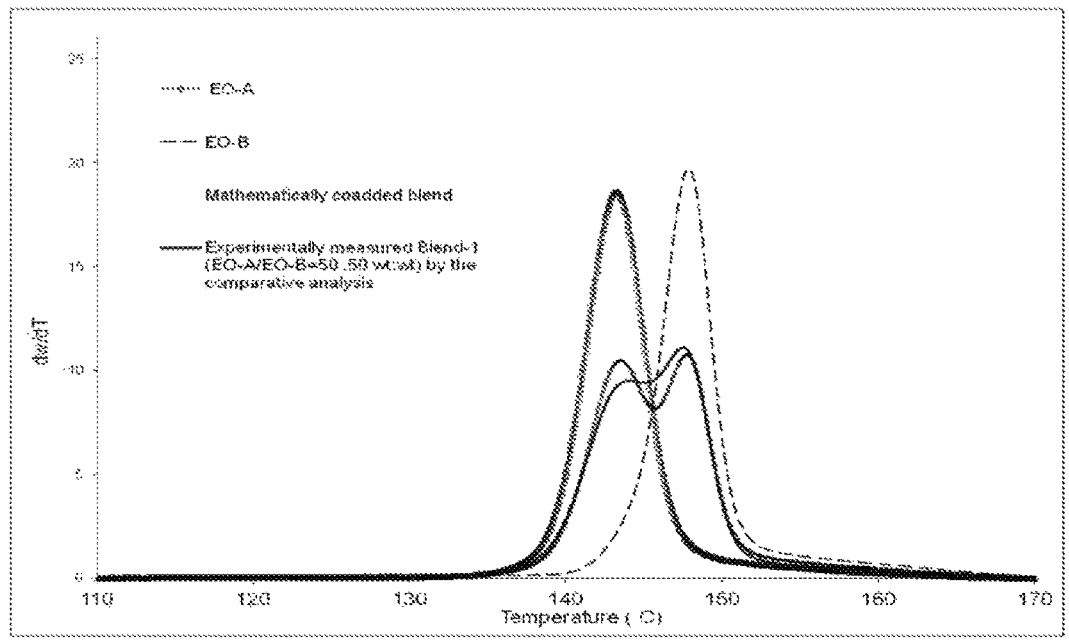
FIG. 8a depicts the HT-TGIC chromatograms of the Sample #1 (EO-A/EO-B=50/50 wt:wt) with the comparative analysis, which is overlaid with the individual polymer components.
Figure 8B:
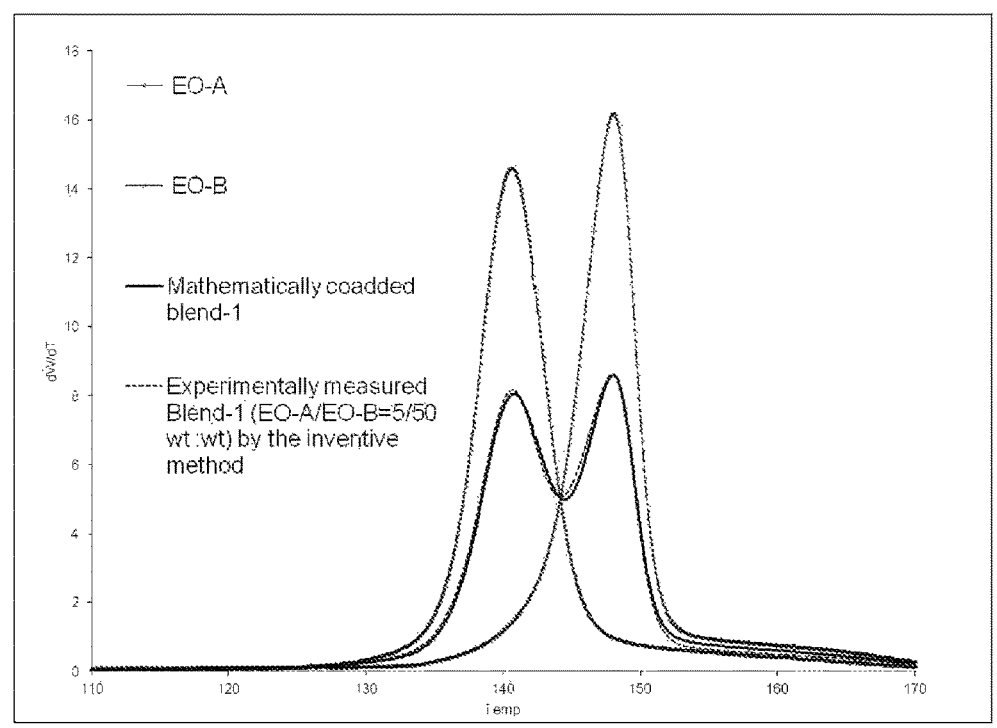
FIG. 8b depicts the HT-TGIC chromatograms of the Sample-1 (EO-A/EO-B=50/50 wt:wt), when total number of cycles=3, which is overlaid with the individual polymer components.

The Sample #1 was analyzed for HT-TGIC using the comparative analysis (the number of cycle, n=0) and inventive analysis (the total number of cycles=3). The detailed experimental parameters are listed in Table 1. The temperature profile of the cooling, heating and eluting steps was shown in FIG. 3. The overlay of the inventive HT-TGIC chromatogram of the Sample #1 obtained experimentally, and the mathematically constructed chromatogram, combined from each individual component analyzed at 2 mg/mL, is shown in FIG. 8a (the comparative analysis) and FIG. 8b (the inventive analysis) with low porosity stationary phase. FIG. 8a clearly shows that the presence of severe co-elution with the comparative analysis, where the mathematically constructed chromatogram does not match with the experimental result in the eluting temperature range of 142 to 148° C. FIG. 8b shows that the inventive method leads to a well matched overlay of the HT-TGIC chromatograms for the Sample #1, obtained mathematically and experimentally, indicating the absence of co-elution in the inventive method.

Study 5 Minimization of Coelution for Sample #2

Figure 9A:
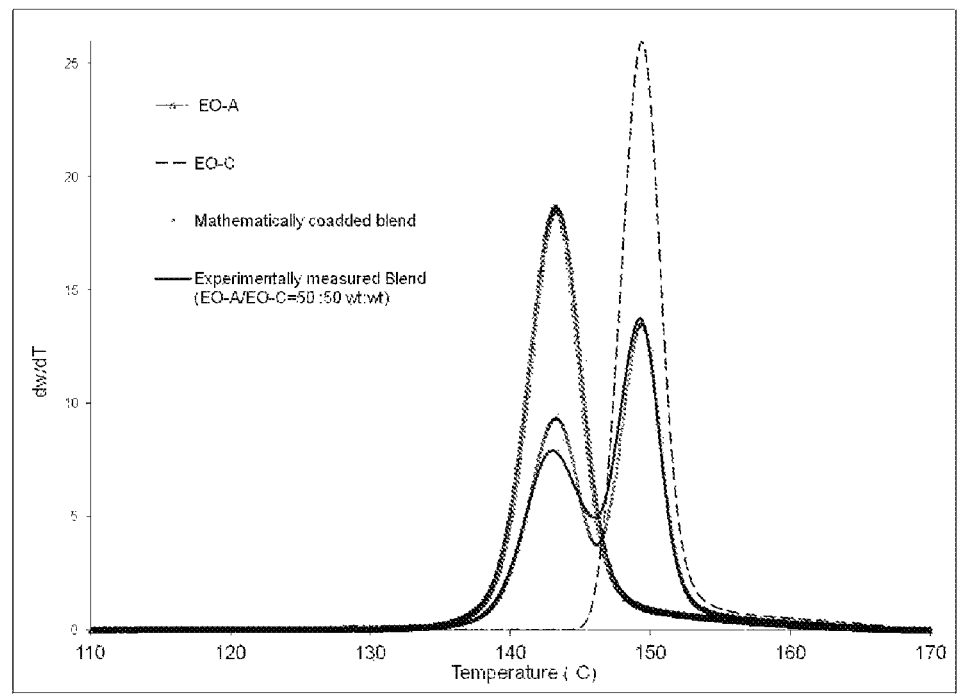
FIG. 9a depicts the HT-TGIC chromatograms of the Sample #2 (EO-A/EO-C=50/50 wt:wt) with the comparative analysis which is overlaid with the individual polymer components.
Figure 9B:
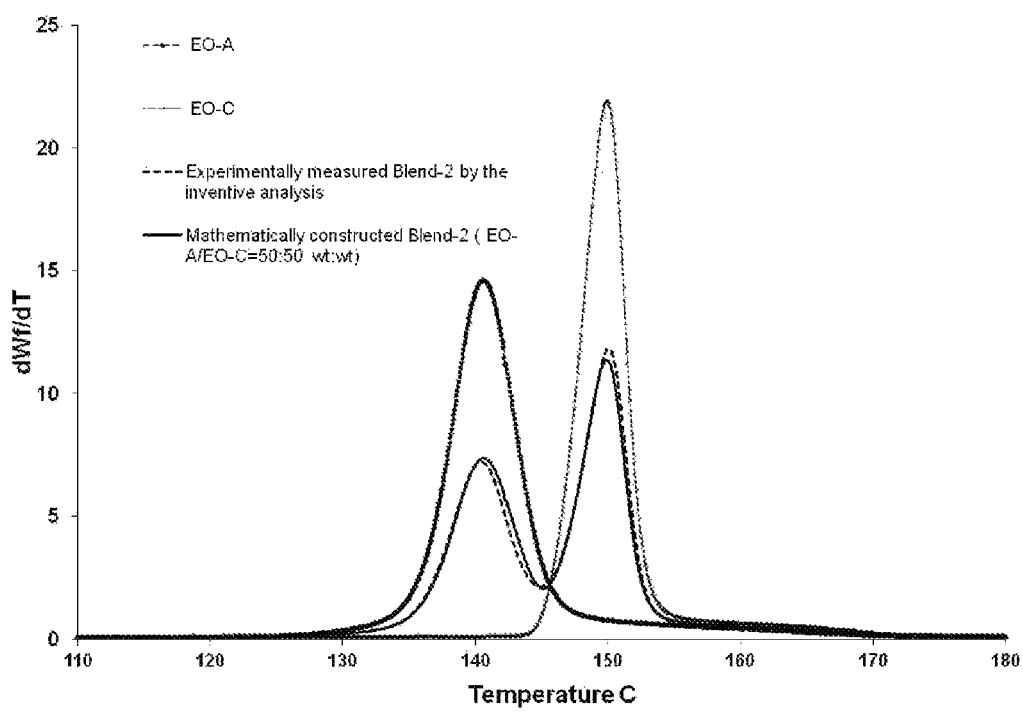
FIG. 9b depicts the HT-TGIC chromatograms of the Sample #2 (EO-A/EO-C=50/50 wt:wt), when total number of cycles=3, which is overlaid with the individual polymer components.

Sample #2 was analyzed by HT-TGIC using the comparative analysis (the number of cycle=0) and inventive analysis (the total number of cycles=3). The detailed experimental parameters are listed in Table 1. The temperature profile of the cooling, heating and eluting steps was shown in FIG. 3. The overlay of HT-TGIC chromatogram of the Sample #1, obtained experimentally, and the mathematically constructed from each individual polymer component, analyzed at 2 mg/mL, is shown in FIG. 9a (the comparative analysis) and in FIG. 9b (the inventive analysis). FIG. 9a clearly shows that the presence of severe co-elution with the comparative analysis at the number of cycle=zero, where the mathematically constructed chromatogram of Sample #2 does not match with the experimental result in the eluting temperature of 143 to 148° C. FIG. 9b shows that the inventive method leads to a well overlaid HT-TGIC chromatogram for the Sample #2, obtained mathematically and experimentally, indicating the absence of co-elution in the inventive method with number of cycle=3.

Study 6 Pore Size Distribution of the Stationary Phase

Figure 10:
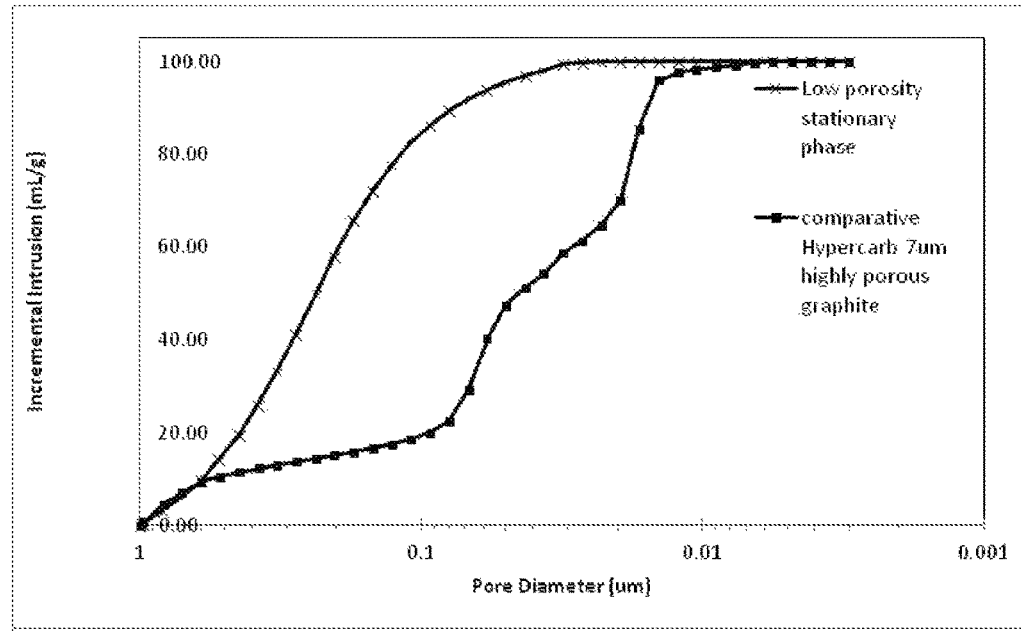
FIG. 10 depicts the cumulative pore size distribution, in the range of 1 to 0.003 microns, for a high porosity stationary phase and a low porosity stationary phase.

A high porosity graphitic stationary phase contained in a HYPERCARB (7 um diameter particle size) column, available from Thermofish Scientific, was isolated. This high porosity graphitic stationary phase (graphite) and a low porosity graphitic stationary phase (graphite) were characterized for pore size distribution and BET surface area measurement. The results are shown in Table 6. The high porosity graphite had a much higher porosity (38.8%) and BET surface area of 154.6 m²/g, versus the low porosity graphite, having 12% porosity and BET surface area of 3.4 m²/g. This indicates that the highly porosity graphite has many more pores than the low porosity graphite (Superior Graphite Co. (USA). FIG. 10 shows the cumulative pore size (pore diameter) distribution in the range of 1 to 0.003 microns. For the high porosity graphite, 78% of the pores had a pore size in the range of 0.1 to 0.01 microns, which contribute to a strong size exclusion effect on the HT-TGIC separation, which, in turn, worsen the separation by HT-TGIC when a multiple numbers of cycles are used (see FIG. 6 and FIG. 7).

TABLE 6

Pore size distribution and surface area characterization of the inventive stationary phase and the comparative stationary phase (HYPERCARB 7 microns).

| | Total Pore Area (m2/g) | Bulk Density (g/mL) | Apparent Skeletal Density (g/mL) | Porosity (%)* | BET Surface Area (m2/g) |
|---|---|---|---|---|---|
| high porosity stationary phase | 154.6 | 0.314 | 0.51 | 38.1 | 122.1 |
| low porosity stationary phase | 3.4 | 0.876 | 1.00 | 12.2 | 5.8 |

*Measured by mercury porosimetry, as described above.

The invention claimed is:

1. A method to increase of the Resolution Index (RI) of a chromatogram generated from a polymer sample comprising at least two olefin-based polymers of different microstructures and/or at least two olefin-based polymer fractions of different microstructures;

said method comprising at least the following steps, and wherein one of A) or B) occurs:

A) n'=0, and steps d) and e) below are skipped, such that step f) follows step c), and wherein $T3_0$ is greater than $T1_0$;

B) n' is an integer≥1; steps d) and e) are not skipped; and steps d) and e) are repeated for n'−1 times for n'>1;

a1) dissolving the polymer sample in at least one solvent to form a polymer solution;

a2) injecting at least a portion of the polymer solution onto a stationary phase at a temperature $T1_0$ (in ° C.), and wherein no eluent flow through the stationary phase;

b) setting a constant eluent flow rate ($FR_0$) through the stationary phase, while simultaneously cooling the stationary phase at a cooling rate $CR_0$, to a minimum temperature $T2_0$ (in ° C.), where $T2_0<T1_0$; and wherein the flow of the eluent through the stationary phase is stopped at temperature $T2_0$;

c) when the temperature reaches $T2_0$, optionally maintaining the temperature at $T2_0$ for a time $t_{20}$; increasing the temperature of the stationary phase to $T3_0$, at a heating rate $HR_0$, where $T3_0>T2_0$, while maintaining no flow of eluent through the stationary phase; and when the temperature reaches temperature $T3_0$, maintaining no flow rate through the stationary phase for a time $t_{30}$; and maintaining the temperature at $T3_0$ for the time $t_{30}$;

wherein for steps d) and e) below, at each n value, where n is from 1 to n', the eluent flow rate of step d) is $FR_n$; and wherein at least one $T3_n$ (for n≥1) is greater than $T1_0$;

d) setting a constant eluent flow rate ($FR_n$) through the stationary phase, while simultaneously cooling the stationary phase at a rate $CR_n$, to a minimum temperature $T2_n$, where $T2_n<T3_{n-1}$; and wherein the flow of the eluent through the stationary phase is stopped at temperature $T2_n$;

e) when the temperature reaches $T2_n$, optionally maintaining the temperature at $T2_n$ for a time $t_{2n}$; increasing the temperature of the stationary phase to $T3_n$, at a heating rate $HR_n$, where $T3_n>T2_n$, while maintaining no flow of eluent through the stationary phase; and when the temperature reaches temperature $T3_n$, maintaining no flow rate through the stationary phase for a time $t_{3n}$; and maintaining the temperature of the stationary phase at $T3_n$ for the time $t_{3n}$;

f) setting a constant eluent flow rate ($FR_f$) through the stationary phase, while simultaneously cooling the stationary phase at a rate $CR_f$ to a temperature $T2_f$, and when the temperature reaches temperature $T2_f$, optionally maintaining the temperature at $T2_f$ for a time $t_{2f}$;

g) increasing the flow rate (FRe) of the eluent through the stationary phase at a rate of at least 0.1 ml/min, while increasing the temperature of the stationary phase to $T_f$ ($T_f>T2_f$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the chromatogram; and wherein the resolution index (RI)=((RC−R0)/R0)×100; and where RI>zero; and wherein RC is the difference in the elution times of two peak height maximums on the chromatogram; and wherein R0 is the difference in the elution times of the same two peaks height maximums selected for the determination of RC, and wherein these two peak height maximums are present on a comparative chromatogram, generated under the same conditions as the chromatogram for RC, except that the following steps were used in the analysis:

c1) injecting at least a portion of the polymer solution onto a stationary phase at a temperature $T1_0$ (in ° C.), and wherein no eluent flow through the stationary phase;

c2) setting a constant eluent flow rate ($FR_0$) through the stationary phase, while simultaneously cooling the stationary phase at a cooling rate $CR_0$, to a minimum temperature $T2_0$ (in ° C.), where $T2_0<T1_0$; and wherein the flow of the eluent through the stationary phase is stopped at temperature $T2_0$, optionally maintaining the temperature at $T2_0$ for a period $t_{20}$;

c3) increasing the flow rate (FRe) of the eluent through the stationary phase at a rate of at least 0.1 ml/min, while increasing the temperature of the stationary phase to $T_f$ ($T_f>T2_0$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the comparative chromatogram; and wherein the stationary phase has a porosity of less than, or equal to, 20%.

2. The method of claim 1, wherein n'≥1, and for each n value, where n is from 1 to n', a TLVSP (calculated) meets the following Equation B:

$$TLVSPcalc. = \frac{T1_0 - T2_0}{CR_0} * FR_0 + \left\{\sum_1^{n'}\left[\frac{T3_i - T2_i}{CR_i} * FR_i\right]\right\} + \frac{T3_n - T2_f}{CR_f} * FR_f, \quad \text{(EQN B)}$$

wherein i=1 to n', and n'≥1; TLVSP (calculated) is the calculated Total Liquid Volume of the Stationary Phase (in units of "ml"); and wherein TLVSP (calculated)≤TLVSP (measured); wherein TLVSP (measured) is the measured Total Liquid Volume of the Stationary Phase (in units of "ml").

3. The method of claim 1, wherein n'=0, and a TLVSP (calculated) meets the following Equation A:

$$TLVSPcalc. = \frac{T1_0 - T2_0}{CR_0} * FR_0 + \frac{T3_0 - T2_f}{CR_f} * FR_f, \quad \text{(EQN A)}$$

wherein TLVSP (calculated) is the calculated Total Liquid Volume of the Stationary Phase (in units of "ml"); and wherein TLVSP (calculated)≤TLVSP (measured); wherein TLVSP (measured) is the measured Total Liquid Volume of the Stationary Phase (in units of "ml").

4. The method of claim 1, wherein the RI is greater than 5%.

5. The method of claim 1, wherein the stationary phase has a BET surface area less than, or equal to, 10.0 $m^2/g$.

6. The method of claim 1, wherein n' is from 1 to 10.

7. The method of claim 1, wherein the at least two olefin-based polymers have different short chain branching distributions and/or at least two olefin-based polymer fractions have different short chain branching distributions.

8. The method of claim 1, wherein the polymer sample comprises at least two olefin-based polymers, and wherein each olefin-based polymer is independently selected from the following: an ethylene-based polymer or a propylene-based polymer.

9. The method of claim 1, wherein the chromatogram is generated using HT-TGIC.

10. A method to increase of the Resolution Index (RI) of a chromatogram generated from a polymer sample comprising at least two olefin-based polymers of different microstructures and/or at least two olefin-based polymer fractions of different microstructures;

said method comprising at least the following steps, and wherein one of A) or B) occurs:
A) n'=0, and steps d) and e) below are skipped, such that step f) follows step c), and wherein $T3_0$ is greater than $T1_0$;
B) n' is an integer≥1; steps d) and e) are not skipped; and steps d) and e) are repeated for n'−1 times for n'>1;
a1) dissolving the polymer sample in at least one solvent to form a polymer solution;
a2) injecting at least a portion of the polymer solution onto a stationary phase at a temperature $T1_0$ (in ° C.), and wherein no eluent flow through the stationary phase;
b) setting a constant eluent flow rate ($FR_0$) through the stationary phase, while simultaneously cooling the stationary phase at a cooling rate $CR_0$, to a minimum temperature $T2_0$ (in ° C.), where $T2_0 < T1_0$; and wherein the flow of the eluent through the stationary phase is stopped at temperature $T2_0$;
c) when the temperature reaches $T2_0$, optionally maintaining the temperature at $T2_0$ for a time $t_{20}$; increasing the temperature of the stationary phase to $T3_0$, at a heating rate $HR_0$, where $T3_0 > T2_0$, while maintaining no flow of eluent through the stationary phase; and when the temperature reaches temperature $T3_0$, maintaining no flow rate through the stationary phase for a time $t_{30}$; and maintaining the temperature at $T3_0$ for the time $t_{30}$;
wherein for steps d) and e) below, at each n value, where n is from 1 to n', the eluent flow rate of step d) is $FR_n$; and wherein at least one $T3_n$ (for n≥1) is greater than $T1_0$;
d) setting a constant eluent flow rate ($FR_n$) through the stationary phase, while simultaneously cooling the stationary phase at a rate $CR_n$, to a minimum temperature $T2_n$, where $T2_n < T3_{n-1}$; and wherein the flow of the eluent through the stationary phase is stopped at temperature $T2_n$;
e) when the temperature reaches $T2_n$, optionally maintaining the temperature at $T2_n$ for a time $t_{2n}$; increasing the temperature of the stationary phase to $T3_n$, at a heating rate $HR_n$, where $T3_n > T2_n$, while maintaining no flow of eluent through the stationary phase; and when the temperature reaches temperature $T3_n$, maintaining no flow rate through the stationary phase for a time $t_{3n}$; and maintaining the temperature of the stationary phase at $T3_n$ for the time $t_{3n}$;
f) setting a constant eluent flow rate ($FR_f$) through the stationary phase, while simultaneously cooling the stationary phase at a rate $CR_f$, to a temperature $T2_f$, and when the temperature reaches temperature $T2_f$, optionally maintaining the temperature at $T2_f$ for a time $t_{2f}$;
g) increasing the flow rate (FRe) of the eluent through the stationary phase at a rate of at least 0.1 ml/min, while increasing the temperature of the stationary phase to $T_f$ ($T_f > T2_f$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the chromatogram; and
wherein the resolution index (RI)=((RC−R0)/R0)×100; and where RI>zero; and wherein RC is the difference in the elution times of two peak height maximums on the chromatogram; and
wherein R0 is the difference in the elution times of the same two peaks height maximums selected for the determination of RC, and wherein these two peak height maximums are present on a comparative chromatogram, generated under the same conditions as the chromatogram for RC, except that the following steps were used in the analysis:
c1) injecting at least a portion of the polymer solution onto a stationary phase at a temperature $T1_0$ (in ° C.), and wherein no eluent flow through the stationary phase;

c2) setting a constant eluent flow rate ($FR_0$) through the stationary phase, while simultaneously cooling the stationary phase at a cooling rate $CR_0$, to a minimum temperature $T2_0$ (in ° C.), where $T2_0 < T1_0$; and wherein the flow of the eluent through the stationary phase is stopped at temperature $T2_0$, optionally maintaining the temperature at $T2_0$ for a period $t_{20}$;

c3) increasing the flow rate (FRe) of the eluent through the stationary phase at a rate of at least 0.1 ml/min, while increasing the temperature of the stationary phase to $T_f$ ($T_f > T2_0$ and $T_f \geq T1_0$), and eluting the polymer sample from the stationary phase during this temperature increase; and when the stationary phase reaches temperature $T_f$, optionally maintaining the temperature at $T_f$ for a time $t_f$; and generating the comparative chromatogram; and wherein the stationary phase has a BET surface area less than, or equal to, 10.0 m²/g.

11. The method of claim 10, wherein n'≥1, and for each n value, where n is from 1 to n', a TLVSP (calculated) meets the following Equation B:

$$TLVSPcalc. = \frac{T1_0 - T2_0}{CR_0} * FR_0 + \left\{ \sum_1^{n'} \left[ \frac{T3_i - T2_i}{CR_i} * FR_i \right] \right\} + \frac{T3_n - T2_f}{CR_f} * FR_f, \quad \text{(EQN B)}$$

wherein i=1 to n', and n'≥1; TLVSP (calculated) is the calculated Total Liquid Volume of the Stationary Phase (in units of "ml"); and wherein TLVSP (calculated)≤TLVSP (measured); wherein TLVSP (measured) is the measured Total Liquid Volume of the Stationary Phase (in units of "ml").

12. The method of claim 10, wherein n'=0, and a TLVSP (calculated) meets the following Equation A:

$$TLVSPcalc. = \frac{T1_0 - T2_0}{CR_0} * FR_0 + \frac{T3_0 - T2_f}{CR_f} * FR_f, \quad \text{(EQN A)}$$

wherein TLVSP (calculated) is the calculated Total Liquid Volume of the Stationary Phase (in units of "ml"); and wherein TLVSP (calculated)≤TLVSP (measured); wherein TLVSP (measured) is the measured Total Liquid Volume of the Stationary Phase (in units of "ml").

13. The method of claim 10, wherein the RI is greater than 5%.

14. The method of claim 10, wherein n' is from 1 to 10.

15. The method of claim 10, wherein the at least two olefin-based polymers have different short chain branching distributions and/or at least two olefin-based polymer fractions have different short chain branching distributions.

16. The method of claim 10, wherein the polymer sample comprises at least two olefin-based polymers, and wherein each olefin-based polymer is independently selected from the following: an ethylene-based polymer or a propylene-based polymer.

17. The method of claim 10, wherein the chromatogram is generated using HT-TGIC.

* * * * *